(12) United States Patent
Singh

(10) Patent No.: US 9,173,903 B2
(45) Date of Patent: Nov. 3, 2015

(54) FLUID ASSOCIATED WITH ADULT STEM CELLS FOR MEDICAL, COSMETIC, AND VETERINARY USE

(76) Inventor: Ashok K. Singh, Lombard, IL (US)

( * ) Notice: Subject to any disclaimer, the term of this patent is extended or adjusted under 35 U.S.C. 154(b) by 416 days.

(21) Appl. No.: 12/855,760

(22) Filed: Aug. 13, 2010

(65) Prior Publication Data

US 2011/0038903 A1   Feb. 17, 2011

Related U.S. Application Data

(60) Provisional application No. 61/342,154, filed on Apr. 12, 2010, provisional application No. 61/274,372, filed on Aug. 17, 2009.

(51) Int. Cl.

| | | |
|---|---|---|
| *A61P 25/00* | (2006.01) | |
| *A61P 3/10* | (2006.01) | |
| *A61K 9/00* | (2006.01) | |
| *A61P 29/00* | (2006.01) | |
| *A61Q 19/08* | (2006.01) | |
| *A61M 1/00* | (2006.01) | |
| *C12N 5/02* | (2006.01) | |
| *A61K 9/70* | (2006.01) | |
| *C12N 5/07* | (2010.01) | |
| *A61K 35/12* | (2015.01) | |
| *A61K 38/18* | (2006.01) | |
| *A61K 8/02* | (2006.01) | |
| *A61P 17/02* | (2006.01) | |
| *A61K 39/00* | (2006.01) | |
| *A61P 9/00* | (2006.01) | |
| *A61P 37/04* | (2006.01) | |
| *A61K 35/24* | (2015.01) | |

(52) U.S. Cl.
CPC ..................................... *A61K 35/24* (2013.01)

(58) Field of Classification Search
CPC .................................................... A61K 35/12
See application file for complete search history.

(56) References Cited

U.S. PATENT DOCUMENTS

| | | | |
|---|---|---|---|
| 4,520,107 A | 5/1985 | Healy et al. | |
| 5,409,827 A | 4/1995 | Kern | |
| 5,426,045 A | 6/1995 | Sawyer et al. | |
| 5,443,984 A | 8/1995 | Sawyer et al. | |
| 5,695,998 A | 12/1997 | Badylak et al. | |
| 6,264,992 B1 | 7/2001 | Voytik-Harbin et al. | |
| 6,413,772 B1 | 7/2002 | Block | |
| 6,459,917 B1 | 10/2002 | Gowda et al. | |
| 6,558,949 B2 | 5/2003 | Min et al. | |
| 6,562,621 B1 | 5/2003 | Sawyer et al. | |
| 6,599,740 B2 | 7/2003 | Sawyer et al. | |
| 2003/0161817 A1 | 8/2003 | Young et al. | |
| 2004/0166096 A1 | 8/2004 | Kolkin et al. | |
| 2005/0013870 A1 | 1/2005 | Freyman et al. | |
| 2005/0076396 A1 | 4/2005 | Katz et al. | |
| 2005/0153441 A1 | 7/2005 | Hedrick et al. | |
| 2005/0153442 A1 | 7/2005 | Katz et al. | |
| 2006/0228341 A1 | 10/2006 | Wilkison et al. | |
| 2007/0110732 A1 | 5/2007 | Johnson | |
| 2007/0141101 A1 * | 6/2007 | Nugent et al. | 424/423 |
| 2009/0180965 A1 | 7/2009 | Freyman et al. | |

FOREIGN PATENT DOCUMENTS

| | | |
|---|---|---|
| EP | 1169052 B1 * | 7/2005 |
| EP | 1 077 253 B1 | 6/2006 |
| WO | WO 95/25164 A1 | 9/1995 |

OTHER PUBLICATIONS

James, Postgrad Med., 76: 457-465, 2000.*
Sneller, Cleveland Clinic Journal of Medicine, 69 (Suppl II): SII40-SII43, 2000.*
Mowa et al., Reproductive Biology and Endocrinology, 6(64): 1-10, 2008.*
Cross et al., Trends in Pharmacological Sciences, 22(4): 201-207, 2001.*
Rubbert-Roth et al., Arthritis Research & Therapy, 11(Suppl1): S1-S12, 2009.*
Sherer et al., Curr. Opin. Rheumatol., 22: 237-245, 2010.*
Black et al., Veterinary Therapeutics, 8(4): 272-284, 2007.*
Domenico Ribatti (2009). Recent Advances in Angiogenesis and Antiangiogenesis, vol. 1: Bentham e Books, p. 23.*
Sanchez et al., Clinical and Experimental Rheumatology, 26: 910-913, 2008.*
Galiano et al., American Journal of Pathology, 164(6): 1935-1947, 2004.*
Greenwood, B., An Implanted Chamber and Catheter for teh Collection of Tissue Wound Fluid from the Sheep, J. of Physiology (Cambridge), vol. 210 No. 2, 1970, pp. 118-119.
Cromack DT, et al., Transforming Growth Factor Beta Levels in Rat Wound Chambers, J. of Surgical Research, Academic Press, Inc., CA, vol. 42, No. 6, Jun. 1987, pp. 622-628.
Robertson, J. Gray, et al., Insulin-like Growth Factor I (IGF-I) and IGF-binding Proteins in Rat Wound Fluid, Endocrinology, vol. 137, No. 7, 1996, pp. 2774-2781.
International Search Report and Written Opinion for International Application PCT/US2010/002241 dated Mar. 3, 2011.
Litbarg, N., et al., Activated omentum becomes rich in factors that promote healing and tissue regeneration, Cell Tissue Res (2007) 328:487-497.

(Continued)

*Primary Examiner* — Thaian N Ton
(74) *Attorney, Agent, or Firm* — Leydig, Voit & Mayer, Ltd.

(57) ABSTRACT

Apparatus and process to create, expand, and localize the population of stem cells in adult tissues by placing a foreign body either in omentum or in the subcutaneous tissue. The apparatus 1) traps the granulation fluid, cells a fluid rich in a myriad of growth factors, 2) mobilizes and concentrates free-floating stem cells in the granulation fluid, and 3) stimulates the growth of a new tissue around the apparatus, which provides another source of stem cells. Stem cells obtained by this process can be used as freshly isolated or after culturing, which can be used for wound healing, treating diseases, and regenerating organs in animals and humans. The granulation fluid could substitute the stem cells in many of their applications and offers the convenience of an injectable medicine for treating animal and human diseases.

35 Claims, 34 Drawing Sheets

(56) References Cited

OTHER PUBLICATIONS

Singh, A., et al., Impaired integration of endothelial progenitor cells in capillaries of diabetic wounds is reversible with VEGF infusion, Translational Research, May 2007, vol. 149, No. 5, pp. 282-291.
Patel, J. et al., Foreign body-induced granulation tissue is a source of adult stem cells, Translational Research, Apr. 2010, vol. 155, No. 4, pp. 191-199.
Gudehithlu, K.P., et al., Antagonism of vascular endothelial growth factor results in microvessel attrition and disorganization of wound tissue, J. Lab Clin Med, Apr. 2005, vol. 145, No. 4, pp. 194-203.
Correspondence from J. Peter Paredes to Kenneth Spina regarding U.S. Appl. No. 12/855,760 dated Dec. 11, 2013 (2 pgs). Redacted.
Correspondence from Jeffrey B. Burgan to J. Peter Paredes regarding U.S. Appl. No. 12/855,760 dated Dec. 12, 2013 (2 pgs). Redacted.
Correspondence from J. Peter Paredes to Jeffrey B. Burgan regarding U.S. Appl. No. 12/855,760 dated Dec. 18, 2013 (3 pgs). Redacted.
Correspondence from Jeffrey B. Burgan to J. Peter Paredes regarding U.S. Appl. No. 12/855,760 dated Jan. 14, 2014 (1 pg). Redacted.
Kreisberg et al., "Isolation and characterization of rat glomerular epithelial cells in vitro," *Kidney International* 14:21-30 (1978).
Litbarg et al., "Activated omentum induces nephrogenesis in surgically wounded kidney," Presented at the Am Soc Nephrology Annual Meeting at Philadelphia, PA, TH-PO019 (Nov. 2008), 1 pg.
Pancholi et al., "Culture of omentum-induced regenerating liver yielded hepatocyte-committed stem cells," *Translational Research*, 156(6): p. 358-368 (2010).
Pancholi et al., "Stellate-Like Mesenchymal Stem Cells Cultured from Omentum-Induced Regenerating Liver Tissue," *Gastroenterology*, 136(5, Suppl. 1): p. A78 (2009).
Pancholi et al., "Stem Cells Cultured From Omentum-Induced Regenerating Liver Can Be Differentiated to Hepatocytes," *Journal of Investigative Medicine*, 58(4): p. 683 (2010).
Patel et al., "Fusion of activated omentum with kidney prevents progression of chronic kidney disease," 2010 Combined Annual Meeting of the Central Society for Clinical Research and the Midwestern Section American Federation for Medical Research, Chicago, IL United States (Apr. 22-23, 2010) *Journal of Investigative Medicine*, 58/4 (654) (2010).
Patel et al., "Stem Cells Isolated and Cultured From Foreign-Body Induced Granulation Tissue," *Journal of Investigative Medicine*, 57(3): p. 531 (2009).
Robertson et al., "Insulin-like Growth Factor I (IGF-I) and IGF-Binding Proteins in Rat Wound Fluid," *Endocrinology*, vol. 137, No. 7, pp. 2774-2781 (1996).
Singh et al. "Vascular factors altered in glucose-treated mesangial cells and diabetic glomeruli. Changes in vascular factors impair endothelial cell growth and matrix," *Laboratory Investigation* 84: 597-606 (2004).
Singh et al., "Impaired integration of endothelial progenitor cells in capillaries of diabetic wounds is reversible with vascular endothelial growth factor infusion," *Translational Research*, vol. 149, No. 5, pp. 282-291 (2007).
Singh et al., "Omentum facilitates liver regeneration," *World J Gastroenterology*, 15: 1057-1064 (2009).
Singh et al., "Stromal cells cultured from omentum express pluripotent markers, produce high amounts of VEGF, and engraft to injured sites," *Cell Tiss Res*, 332: 81-88 (2008).
Singh et al., "Transplanting fragments of diabetic pancreas into activated omentum gives rise to new insulin producing cells," *Biochem Biophys Res Comm*, 355: 258-262 (2007).
Vernik et al., "Omentum: Power to heal and regenerate," (Editorial) *Intl J Artif Organs*, 30: 95-99 (2007).
Australian Patent Office, Patent Examination Report No. 1 in Australian Patent Application No. 2010284704 (Jun. 23, 2014).

\* cited by examiner

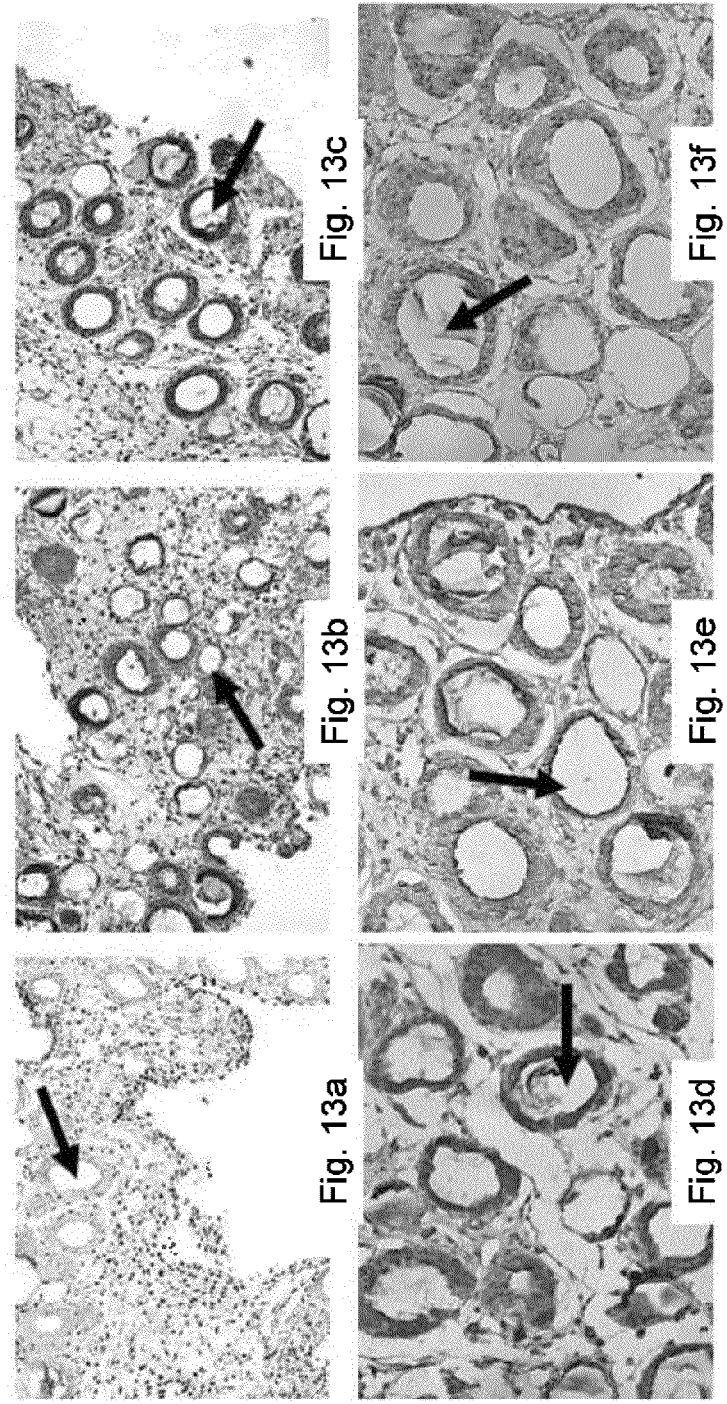

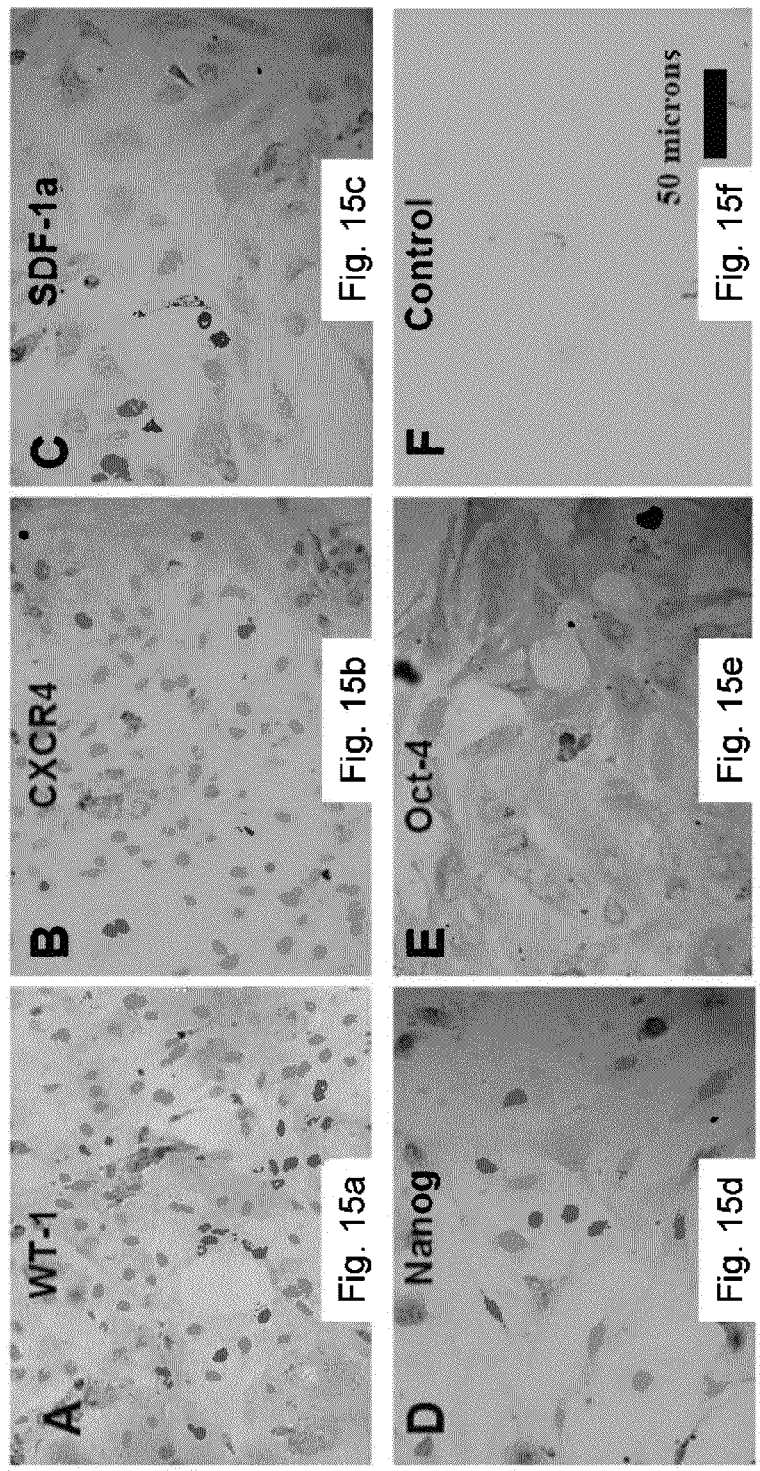

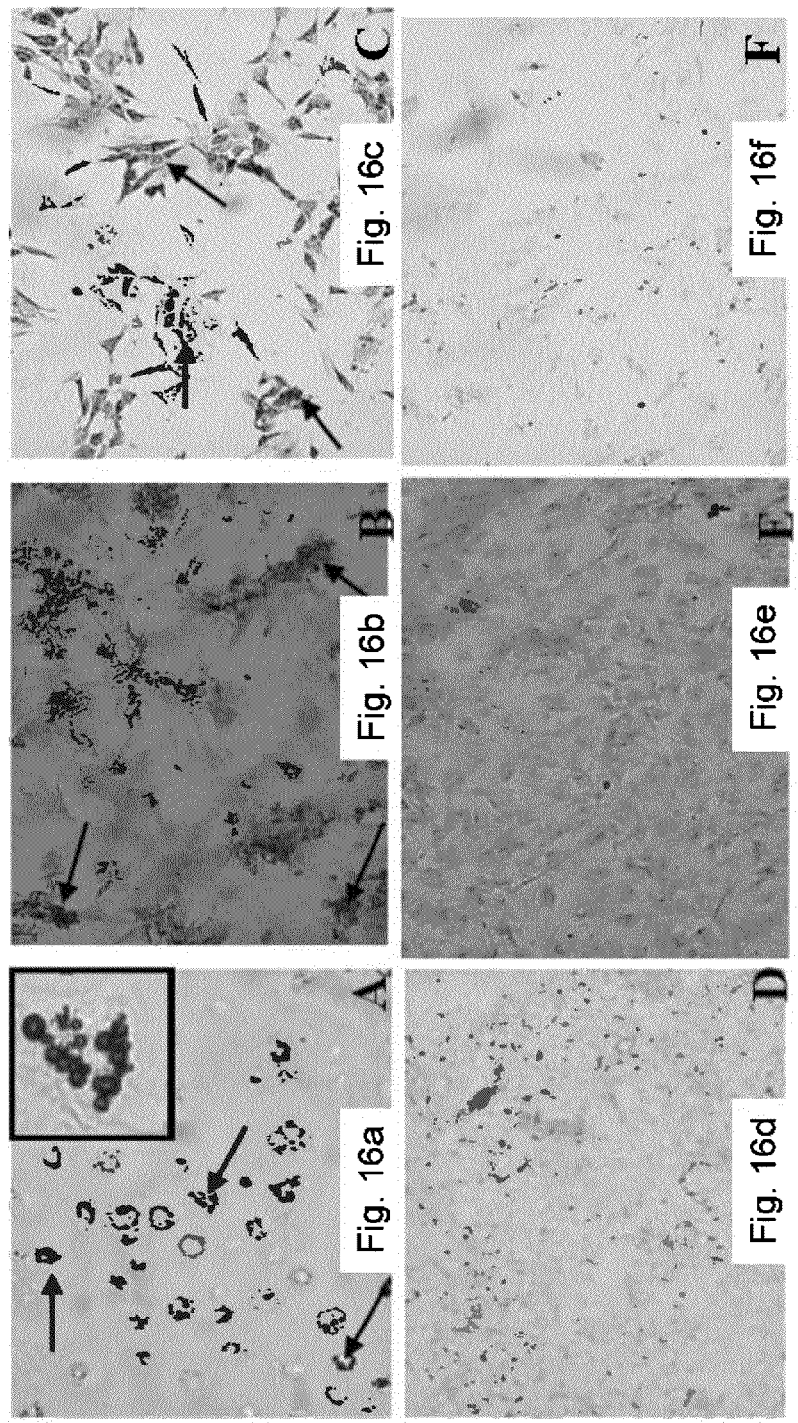

FLUID ASSOCIATED WITH ADULT STEM CELLS FOR MEDICAL, COSMETIC, AND VETERINARY USE

CROSS-REFERENCE TO RELATED APPLICATION

This patent application is a non-provisional application that claims benefit of U.S. provisional application Ser. No. 61/342,154, titled METHOD FOR INDUCING AND HARVESTING A UNIQUE FLUID RICH IN GROWTH FACTORS FROM MAMMALIAN SPECIES BY IMPLANTING A FOREIGH (sic) BODY DEVICE UNDER THE SKIN, filed on Apr. 12, 2010, and U.S. provisional application Ser. No. 61/274,372, titled PROCESS OF CREATING STEM CELLS IN ADULT TISSUES FOR USE IN TISSUE REPAIR AND REGENERATION, filed on Aug. 17, 2009, both are incorporated herein by reference.

FIELD OF THE INVENTION

This invention relates to a design and use of an implant introduced under the skin or in the omentum that creates, in particular, a fluid associated with stem cells rich in natural growth factors that could be harvested and collected within the implant and a tissue abundant in adult stem cells enveloping the exterior of the implant.

BACKGROUND OF THE INVENTION

Fetal bovine serum (FBS) is currently the gold standard in regard to a natural fluid that is rich in a mixture of growth factors. As such FBS is used as an essential ingredient for tissue culture of all types of mammalian cells. The most important commercial uses of FBS are in research and manufacture of viral vaccines for human and animal health. It is obtained from the fetuses of pregnant cows at the time of slaughter. Since the serum is derived from a rapidly growing tissue it is unique in its high content of tissue growth factors and a host of differentiation factors which are responsible for maintaining the natural properties of cells in culture. Even though a reagent of choice, the use of FBS involves the risk of transmission of the mad cow disease via the FBS harvested from infected cows during times of disease outbreak. Further, the method of obtaining FBS by slaughtering unborn calves has raised serious ethical problems, restricting the supply of this essential biomaterial. It is important that a substitute be found that could be less expensive, and avoid slaughtering unborn fetuses.

The cell culture industry is responding to these needs by developing specialized formulations containing manufactured growth factors and other proprietary ingredients tailor-made for culture of specific cells. Despite the addition of known factors, these formulations also contain FBS, albeit in lesser amounts. Presently, such formulations are three to four times more expensive than media made from FBS.

As commonly understood, stem cells are 'mother' cells that can multiply and differentiate to many different types of cells that make up the many organs and tissues. Such stem cells are derived from the blastocyst, a small tissue formed days after conception. Although multipotent, the use of these cells, because of their fetal origin, is opposed by many societies in the world on ethical grounds. Even though their potential power to regenerate all tissues is exciting to researchers their clinical use is at present fraught with safety concerns. The main safety problem with these cells is that when injected these cells become tumors because, at present, the natural cues which exist in a developing fetus cannot be replicated in a patient. Adult stem cells, on the other hand, are derived from adult organs such as bone marrow, fat, hair and other tissues in which they lie in a dormant state. This is currently an active area of research and investigators are finding such cells in more and more tissues. These cells are safer to use because they do not form tumors when injected. Their potency to form other tissues is at present limited to fat, cartilage and bone. Whether they can form other tissue is debatable. However, they have been shown to improve healing and repair damaged and diseased organs. Such knowledge of their potency has mainly come from studies of the bone marrow derived stem cells. It is unclear how the different stem cells obtainable from the various organs compare in their potency to heal and repair damaged tissue. It is therefore important to search for newer sources of adult stem cells because it is possible that an adult stem cell, either lying dormant in a tissue or inducible by experimental means, may be found that could be comparable to the embryonic stem cells in potency and yet be safe to use.

SUMMARY OF THE INVENTION

The present invention generates a reaction that results in new tissue growth around a foreign body when an adult tissue encounters the foreign body. Foreign body, implant, and device are interchangeably used in this application to mean apparatus of the present invention. This reaction occurs to protect the organism from the harmful effects of the foreign substance. In the process of building the new tissue, the body brings or creates stem cells at the site for construction of the tissue. Such stem cells then differentiate into different cell types including epitheloid cells (immediately surrounding the foreign body), fibrocytes (to produce extracellular matrix), blood vessels (to supply blood), pericytes (to support the blood vessels) and many other cell types that are required to build the encapsulating tissue. While the early stem cells (undifferentiated cells) are mostly present inside the device suspended in a fluid (discussed below) the differentiated cells are mostly on the outside of the device in the form of the encapsulating tissue. Foreign body reactions occur in the adult skin (subcutaneous), the omentum (also an adipose tissue) and other fatty tissues such as the epididymis. Examples of foreign bodies used for activating these tissues are inert substances such as polydextran particles, polyacrylamide particles, polyethylene or polyvinyl or other plastic tubes and solid objects made of plastic or foam, and suture threads. As long as the foreign material is particulate, inert and larger than 120 µM in size, it readily creates a new tissue. Particulate material that is smaller than 120 µM in size results in a tissue that is rich in macrophages and giant cells and poor in stem cells.

The quality of stem cells from the foreign body activated adult tissue produced by the present invention can be different from the stem cells isolated from non-activated native tissues such as bone marrow, fat and other adult organs. Since the stem cells from the foreign body induced granulation tissue participate in creating a new tissue, such newly-formed tissues are expected to have more relevant stem cell activity.

The present invention yields two types of stem cells; cells formed as new solid tissue on outside the tube or implant and free-floating cells suspended in the fluid collected inside of the tube. Adult stem cells can be collected using the present invention and used in various applications: direct use of the collected fluid (no further processing), freeze drying collected fluid into powdered form, separating stem cells from solid tissue, and separating free-floating stem cells suspended in the fluid, culturing the solid tissue, either individually or in different combinations could be used for medical, cosmetic and veterinary purposes.

One embodiment of the present invention is an apparatus to trap and collect a fluid which is secreted by the surrounding stem cells, called the granuloma fluid. Granuloma fluid, which is rich in growth factors, can be potentially obtained, using the technique described here, from any adult animal species (pig, cow, horse, sheep and small animals such as dogs, rat, rabbit etc). The present invention induces that generation of granuloma fluid in an adult animal by implanting a foreign-body in the animal. Soon after implantation in the body the foreign body device is rapidly covered by a new tissue. A granuloma fluid accumulates in the device that can be continuously harvested for commercial use. When granuloma fluid is added to a basal tissue culture medium, it was able to support the growth of four different types of rat and human cells, and equals or exceeds FBS in potency. The present invention allows collection of growth factor-rich fluid from adult animals, an advantage over FBS that is harvested from unborn cow fetuses. In addition to the use of granuloma fluid as a substitute for FBS in tissue culture it can be used for many other medical applications where a concentrated mixture of growth factors is required as for treating arthritis, kidney, heart, spinal cord, other organ and systemic diseases/ injuries and as well for cosmetic applications.

Adult tissues created by a foreign body of the present invention are also sites of high angiogenesis, high levels of growth factors and abundance of stem cells making them excellent sites for implanting in vitro engineered organ for cellularization, vascularization, growth, and maturation of the engineered tissue for subsequent transplantation to the appropriate site in the body. The tissue created by a foreign body can also be deliberately brought in contact with injured organs to induce repair and regeneration, such as a paste or topical cream with or without further preparation.

As discussed above, one embodiment of the present invention is a device that is implanted under the skin of mammalian species to induce and trap a plasma-like granuloma fluid that can be continuously harvested for commercial use. The granuloma fluid is a fluid rich in a mix of growth factors and stem cells equals or exceeds in potency compared to fetal bovine serum and is an adequate substitute for FBS. The granuloma fluid collected in this manner can be used for:

1) Culture of mammalian cells;
2) Isolating and purifying growth factors for medical use;
3) Treatment of acute and chronic diseases many of which respond to growth factors, such as diabetes by injection as a fluid for vaccines;
4) In dressings for accelerating healing of skin injuries and surgical wounds and arthritis;
5) In topical and systemic formulations for cosmetic use as anti-aging injections, creams and lotions.

Stem cells obtained from a granulation tissue, either from inside the device as a suspension in the granuloma fluid or from the outside of the device present in the encapsulating tissue, are sources of adult stem cells. Since they are derived from a newly-formed tissue, the cells have a greater relevance as stem cells, unlike other adult stem cells derived from either the bone marrow, fat tissue or other adult organs in which the stem cells are in a dormant state.

BRIEF DESCRIPTION OF THE DRAWINGS

The invention is further illustrated by the following drawings in which:

FIGS. 13a-f are microphotographs of rat omentum activated with polydextran particles (particles are indicated by arrows) and immunostained for adult stem cell and embryonic pluripotent markers showing strong immuno-reactivity for WT-1 (FIG. 13a), SDF-1a (FIG. 13b), and CXCR 4 (adult stem cell markers) (FIG. 13c) and to Nanog (FIG. 13d), Oct-4 (FIG. 13e) and SSEA-1 (embryonic markers) (FIG. 13f).

Figure 14A:
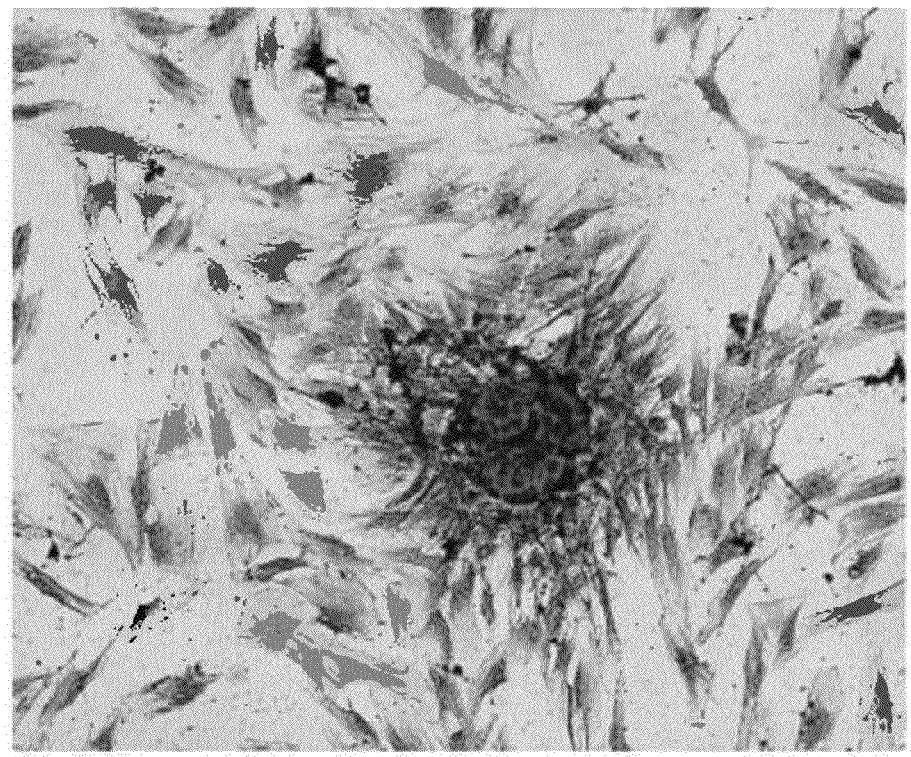
Figure 14B:
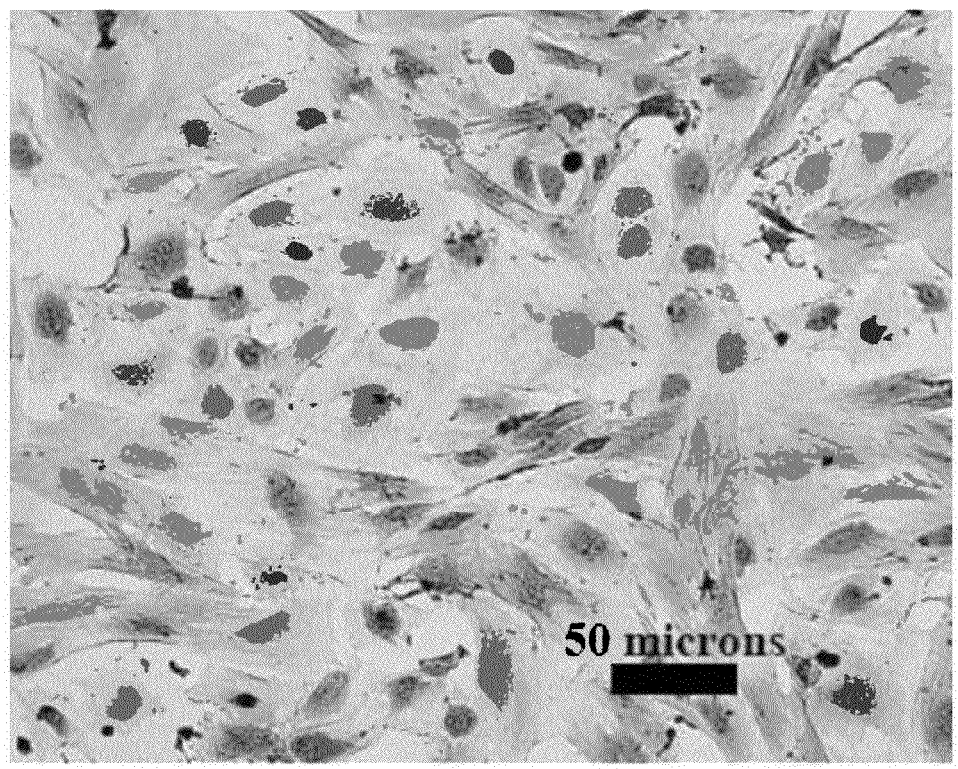
Figure 17A:
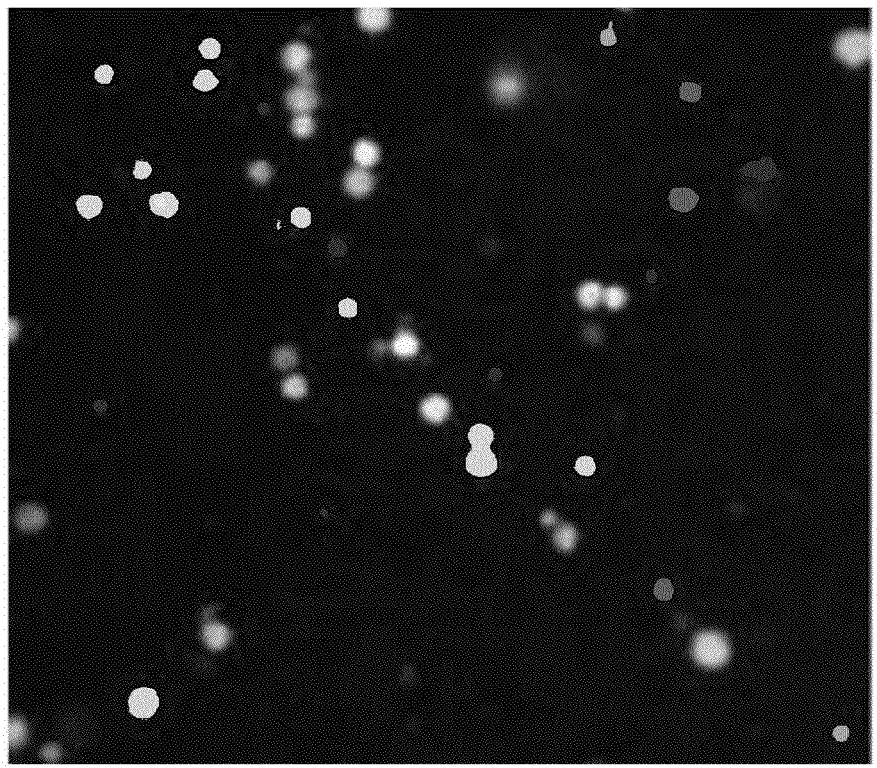
Figure 17B:
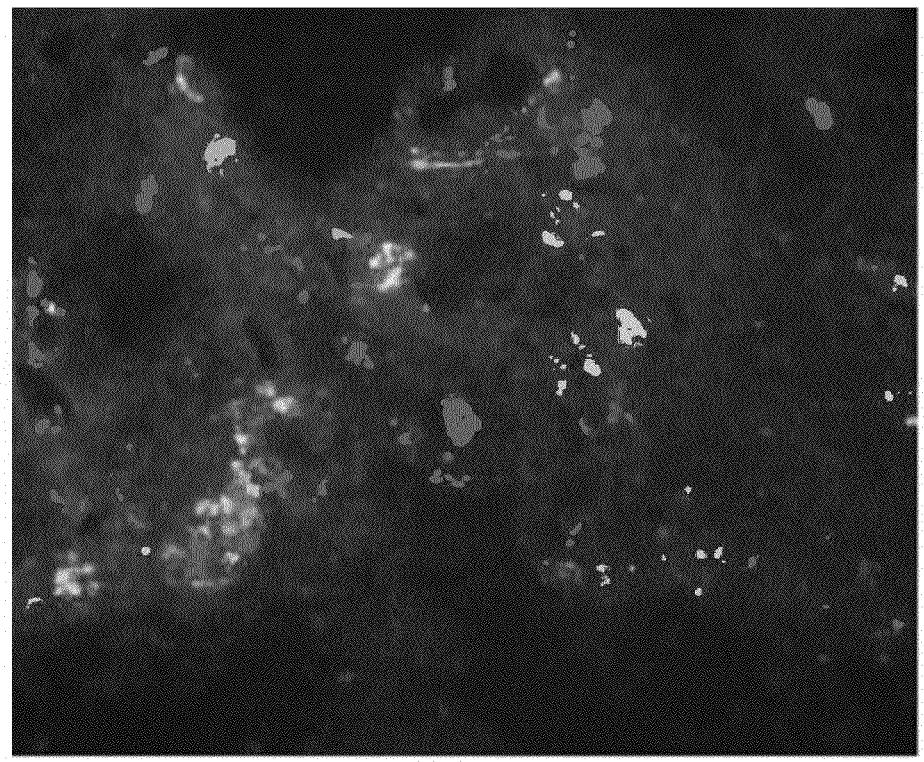
Figure 17C:
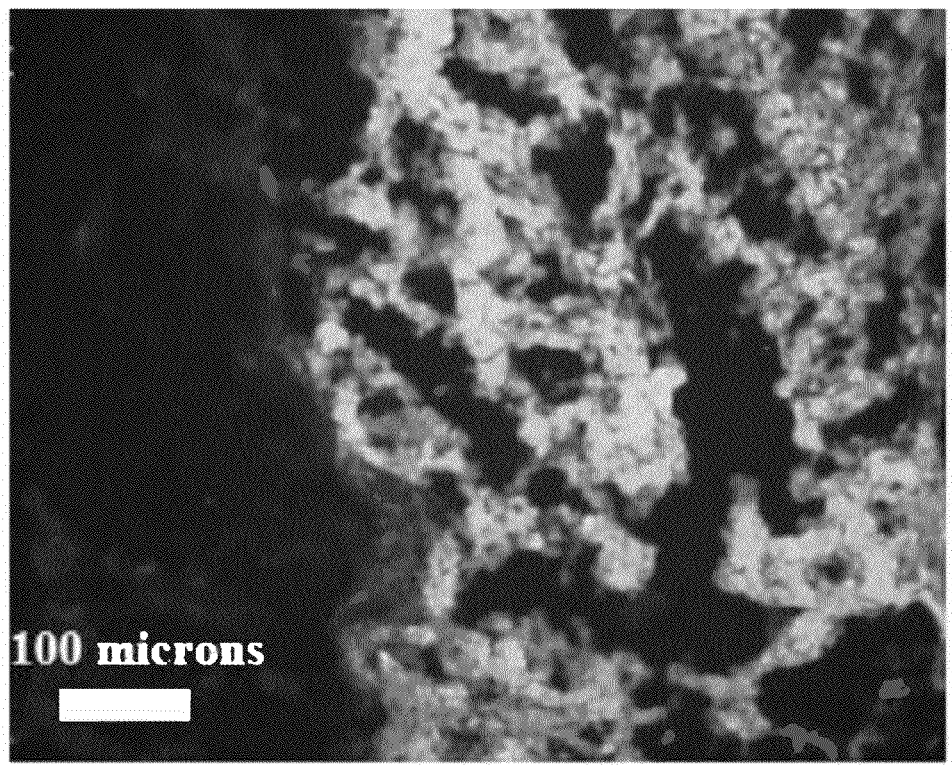
Figure 18A:
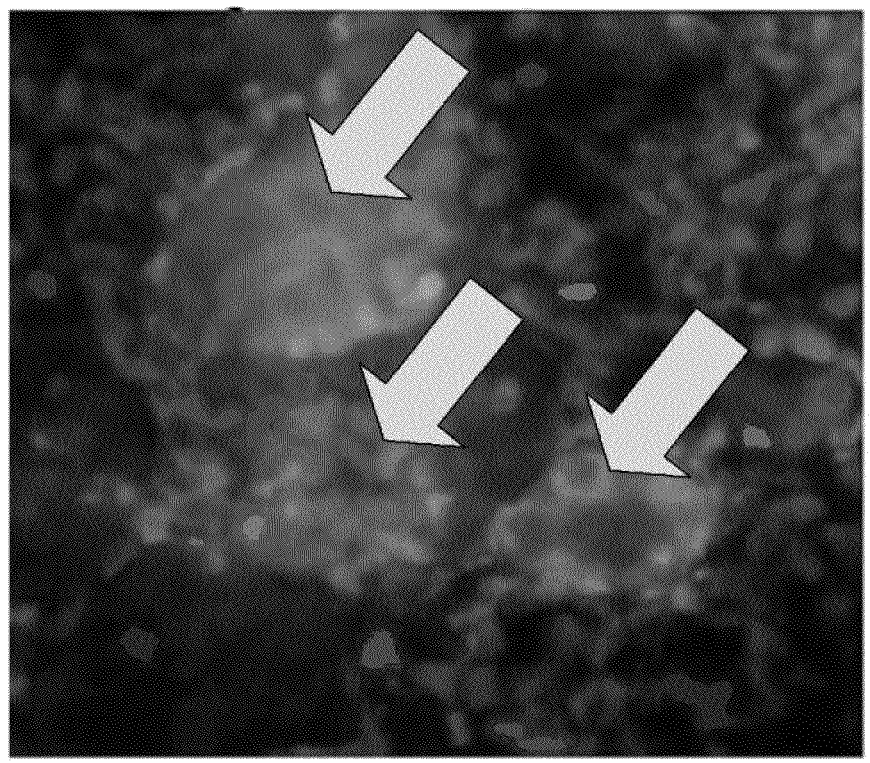
Figure 18B:
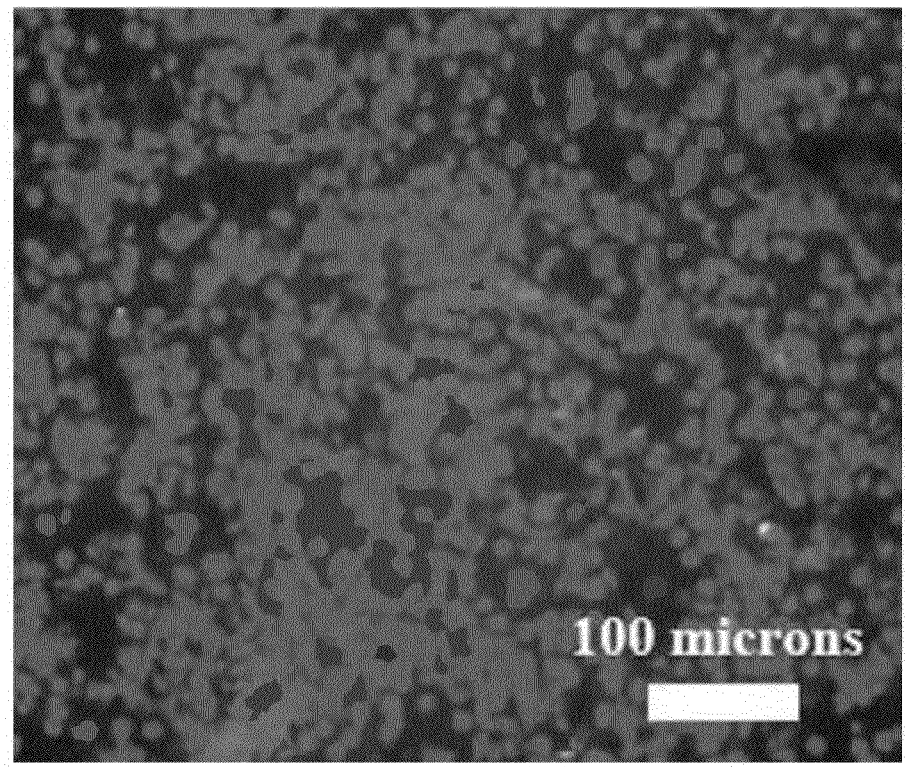
Figure 19:
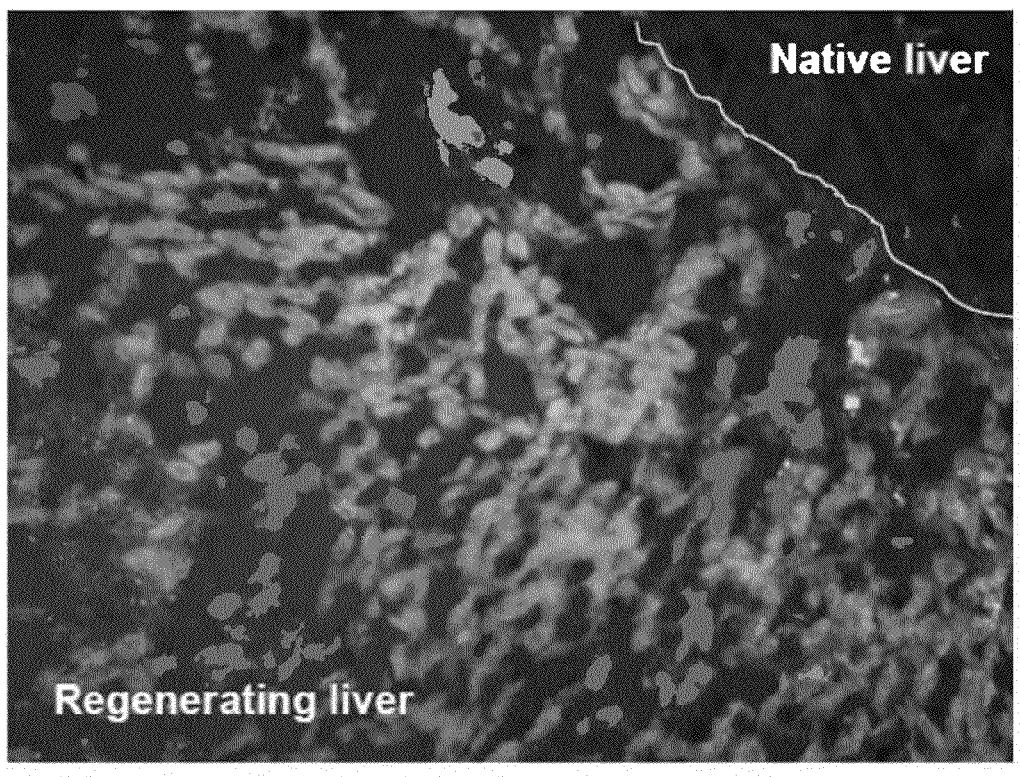
Figure 20:
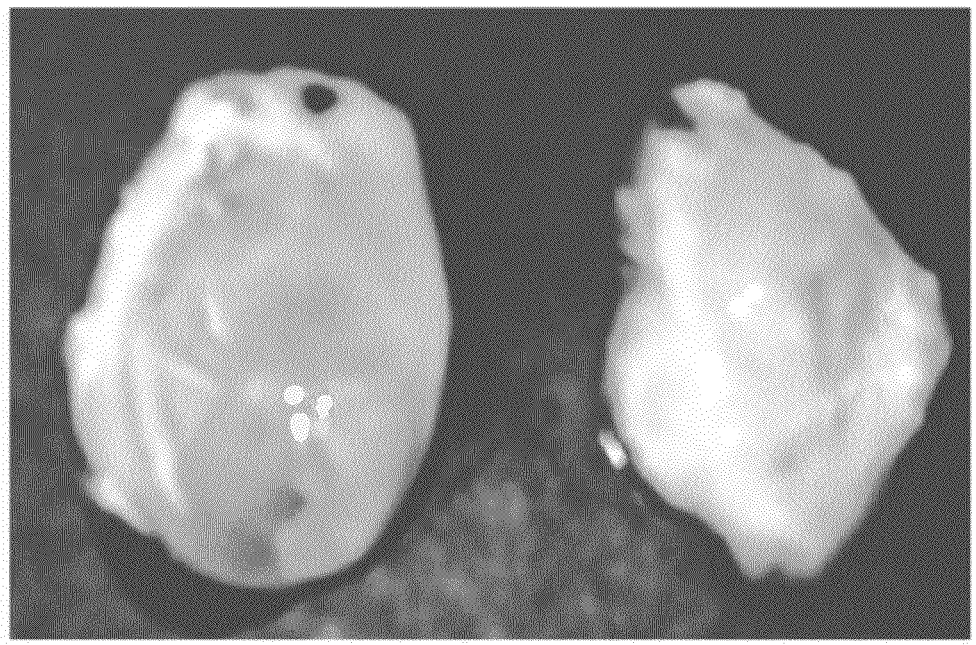
Figure 21A:
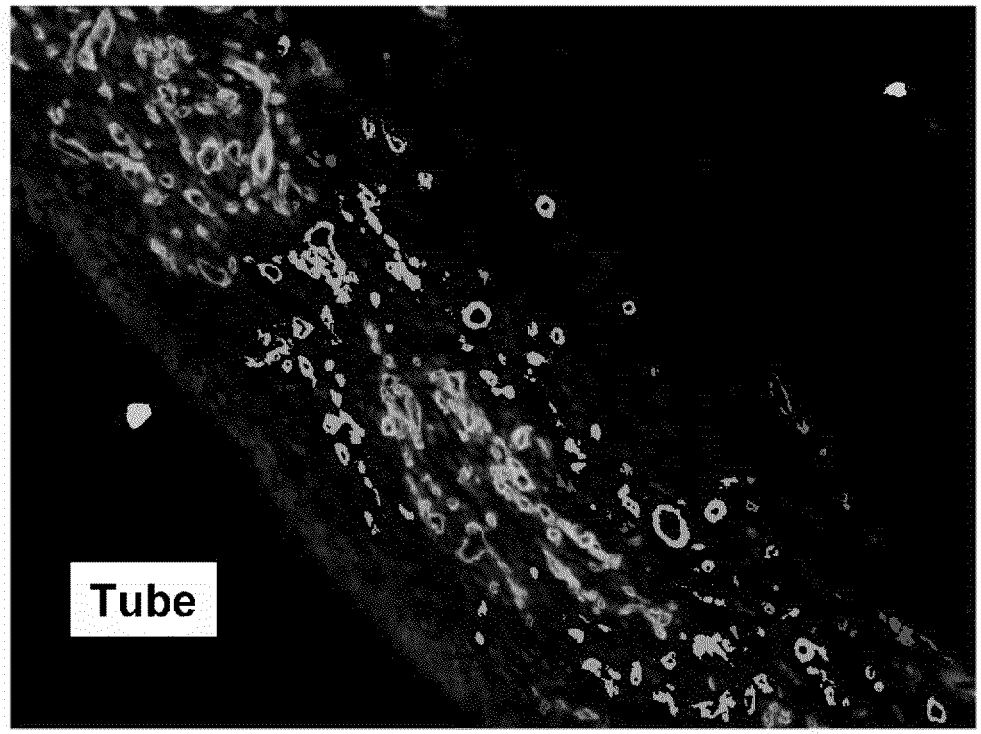
Figure 21B:
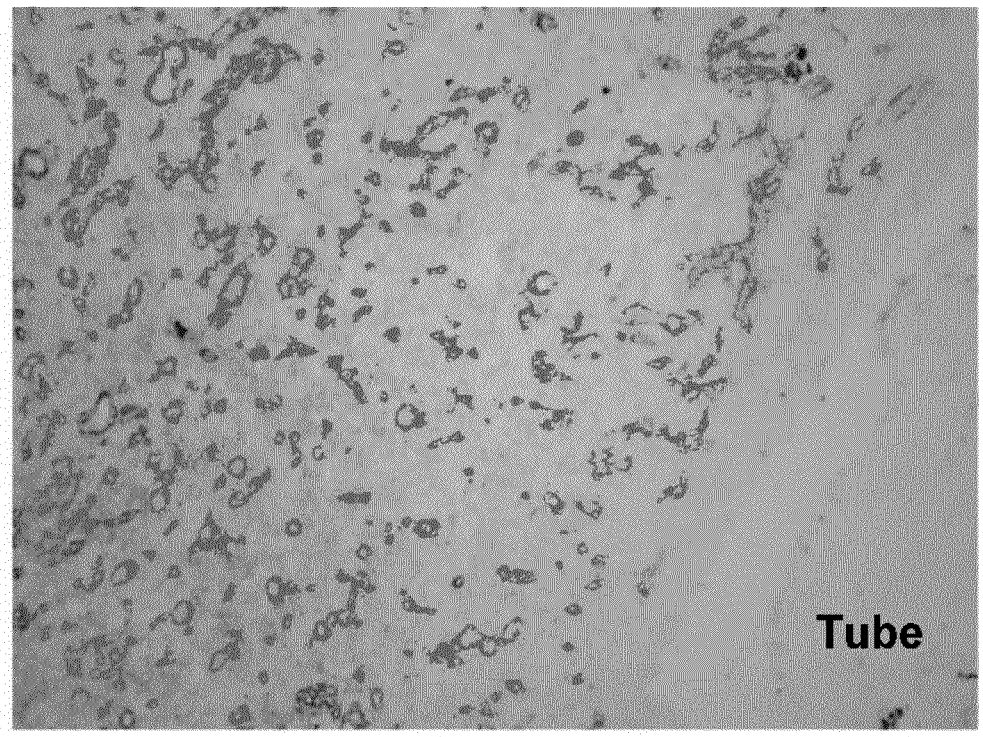

Positive cells (appearing as dark areas) are seen in the immediate layer of cells surrounding the polydextran particles (appearing as open spaces);

FIG. 14a is a microphotograph of omental cells cultured from omentum tissue activated by polydextran particles after 4-5 days in culture showing cells that originally clustered around the polydextran particles started to attach to the dish and multiply (one such particle surrounded by attached cells is shown in the middle of the field);

FIG. 14b is a microphotograph of Passage 3 cultured cells from activated omentum showing robust growth;

FIGS. 15a-f are microphotographs of primary cultures of omental cells stained for adult stem cell markers WT-1 (nuclear) (FIG. 15a), CXCR4 (nuclear) (FIG. 15b), SDF-1a (cytoplasmic) (FIG. 15c), and embryonic pluripotent markers Nanog (FIG. 15d), Oct-4 (FIG. 15e) and SSEA-1 (FIG. 15f) showing that the cultured cells retained their stem cell properties. The cells (appearing as dark areas) continued to express these markers up to 10 generations tested (picture of immune-reactivity at the tenth generation is not shown here); FIG. 15f is a microphotograph of the cultured cell staining showing negative in the absence of first antibody (control);

FIGS. 16a-f are microphotographs of cultured subcutaneous derived stem cells when placed in a specialized medium differentiated in vitro to adipogenic (a: specialized media; d: control media), chondrogenic (b: specialized media; e: control media) and osteogenic (c: specialized media; f: control media) cell types (staining in each case is seen as dark areas in the picture);

FIGS. 17a-c are microphotographs of the migration of cultured omental cells pre-stained by a green dye (a) to a skin wound healing site after local injection (b); control cells injected similarly did not migrate to the wound (c) (stained cells appear white in the picture);

FIGS. 18a-b are microphotographs of the migration of cultured omental cells to injured kidney (a) and not to uninjured kidney (b) after intravenous injection (stained cells appear white in the picture);

FIG. 19 is a microphotograph of a liver tissue 3 days after a resection injury and 24 hours after injection of fluorescently labeled cultured omental cells showing engraftment of the injected cells to the growing liver (stained cells appear white in the picture);

FIG. 20 is a microphotograph illustrating the bladder-like tissue obtained in the rat one week after injection of 5 mL of the polydextran slurry in the subcutaneous tissue; and FIGS. 21a-b are microphotographs of two examples of granulation tissue formed in one week after polyvinyl tube implantation displaying a rich network of micro blood vessels revealed by collagen type IV immune-staining (FIG. 21a immunofluorescent staining (appear white in the picture) and FIG. 21b immuno-peroxidase staining (appear dark in the picture). Tube refers to where the polyvinyl tube was located with respect to the tissue.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

Figure 1A:
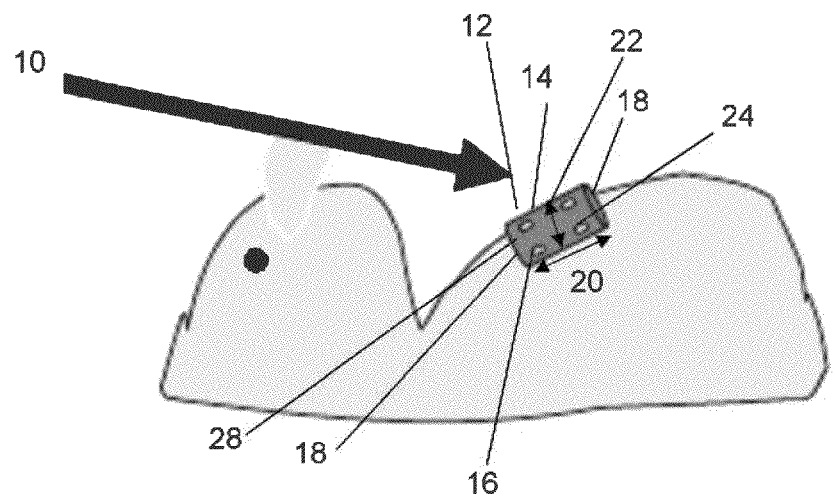
FIGS. 1a-b are pictorial representations of a device of the invention implanted under the skin of an animal (a) showing after one week of the implantation the new tissue that is built around the device (b) could be harvested for isolation and culture of stem cells and the granuloma fluid that collects inside the tube can be harvested frequently (several times a day) for several weeks for other medical and veterinary uses.
Figure 1B:
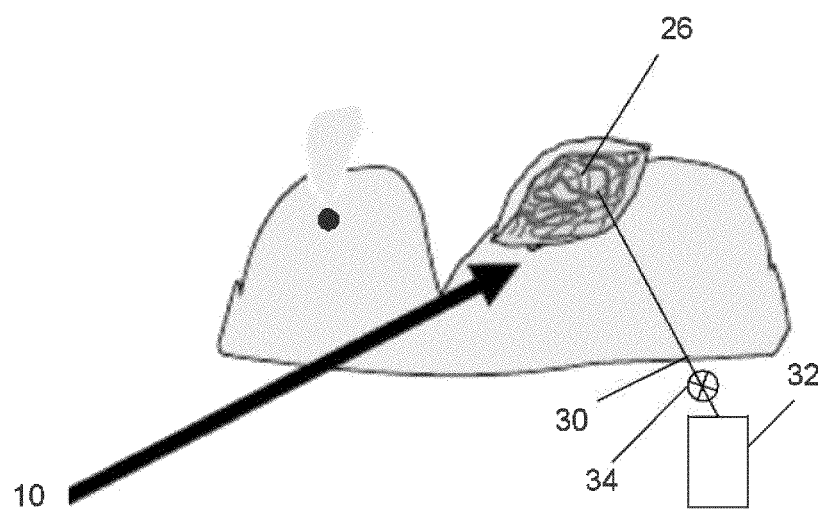

FIGS. 1a and 1b illustrate one embodiment of an granuloma fluid collection apparatus 10 of the present invention to entrap a fluid rich in natural growth factors when implanted under the skin of a donor mammal (such as a rat) to become a foreign body in the donor, as well as a fluid collection device. Apparatus 10 can be made of a piece of non-toxic material, such as a polymer like polythene, polyvinyl or other soft, flexible or hard plastic or metallic material. Apparatus 10 can be tubing 12 having walls 14 include a plurality of holes 16 through walls 14. Ends 18 are sealed to form an enclosed chamber. Any commercially available sealing technique is acceptable, for example by heat application. An example of apparatus 10 made for a rat has length 20 being about 20 mm, diameter 22 being about 7 mm, enclosed chamber volume being about 0.5 ml, and eight holes 16 with a diameter 24 being about 0.5 mm drilled around the tube 12 to allow for steady diffusion and accumulation of surrounding tissue fluid (granuloma fluid) into the enclosed chamber. Granuloma 26 is formed about exterior surface 28 of wall 14. Granuloma 26 forms with new tissue and blood vessels. Granuloma fluid rich in natural growth factors steadily diffuse from granuloma 26 through the plurality of holes 16 for entrapment within the enclosed chamber for harvesting and collecting, either continuously or periodically (semi-continuous). Prior to implantation, apparatus 10 can be stored in 70% alcohol for sterility. Before implantation in the donor, apparatus 10 is washed vigorously with sterile saline and air-dried.

Another possible embodiment to create stem cells and trap the associated fluid is by injecting a slurry of polydextran particles under the skin. The injection of particles under the skin creates a 'bladder-like' granulation tissue with the fluid trapped in the inside of the bladder along with the injected particles. The fluid can be obtained by perforating the bladder and separating the particles by simple centrifugation. The tissue of the bladder provides the source of stem cells. FIG. 20 is a microphotograph showing the bladder-like tissue obtained in the rat one week after injection of 5 mL of the polydextran slurry. The bladder is spherical in shape and the fluid is trapped inside. Granulation tissue formed after one week following injection of 5 mL of polydextran slurry in the subcutaneous tissue. The left image shows the tissue soon after harvesting from the rat. The tissue is like a balloon with the injected polydextran particles and fluid (granulation fluid) enclosed in it. Granulation fluid can be separated after centrifugation and used for various medical applications. The image on the right shows the tissue after the balloon is perforated and the particles and fluid that oozed out have been collected. The tissue is abundant in stem cells and can be processed for use as single cells or for culture.

Other designs using biodegradable or non-biodegradable materials (porous or nonporous) are also contemplated within the scope of the present invention and can also be used with similar results. For example, a piece of foam placed inside the peritoneal cavity also acts as a foreign body and activates the omentum. The omentum expands and grows to occupy the interstices of the foam. After one week the foam can be retrieved. The granuloma fluid gets absorbed by the foam and can be harvested by squeezing the foam. Stem cells from this preparation can be obtained by enzyme treatment (collagenase) of the foam.

As illustrated in FIGS. 1a and 1b, apparatus 10 is surgically implanted into a donor. For illustration purposes, the donor is a Sprague-Dawley rat (males, approx. 300 g) anesthetized with acepromazine prior to the surgical procedure. The implantation location can be shaved and cleaned with alcohol and povidone. Typically, two 1 cm incisions can be made and using blunt dissection to form a subcutaneous pocket around the incision into which apparatus 10 is inserted. One or more apparatus 10 can be implanted into the donor depending on the size of the donor relative to the size of apparatus 10. For illustration purpose herein, two apparatuses 10 are implanted into a donor. The incision was closed with appropriate sutures (such as silk) and the donor is allowed to recover for a period (for example, one week) to form granuloma 26 around apparatus 10 (FIG. 1b). The granuloma 26 is a rapidly growing new tissue with an abundant supply of new blood vessels as seen in FIGS. 21a-b.

Other embodiments of apparatus 10 of the present invention are perforated bags and sheets made of polythene or other non-toxic material may also produce an enclosed pocket (after granuloma formation) for trapping and harvesting of tissue fluid.

A further embodiment of the present invention injects inert particles in the peritoneal cavity that induce a growth factor-rich fluid by the same principle.

One method of harvesting or collecting granuloma fluid from apparatus 10 in a donor (such as a rat) is performed aseptically by a syringe needle having an appropriate gauge (such as gauge #25) by piercing the skin and hole 16 of wall 14 of apparatus 10 and aspirating fluid from the enclosed chamber. The harvesting or collecting of granuloma fluid can occur at any time. For illustration purposes, a period of 4-7 days can be allowed for the formation of granuloma 26 about the exterior surface 28 of wall 14 and diffusion before the granuloma fluid accumulates in the enclosed chamber.

Another method of harvesting can be used in a commercial setting for continuous or semi-continuous fluid collection. Fluid yield can be increased by implanting an appropriately size apparatus 10 in large animal that is constructed in a manner that fluid can be continuously directed and collected at a steady rate through aspiration tube 30 into a sterile bag or suitable container 32 placed outside the donor's body either by gravity (as shown in FIG. 1b) or by mild vacuum generated by a pump (not shown) disposed in tube 30 between apparatus 10 and container 32. Valve 34 can be disposed in aspiration tube 30 or operably connected to container 32 to stop the continuous flow (semi-continuous flow) of granuloma fluid for replacement or emptying of the granuloma fluid from container 32.

Figure 2:
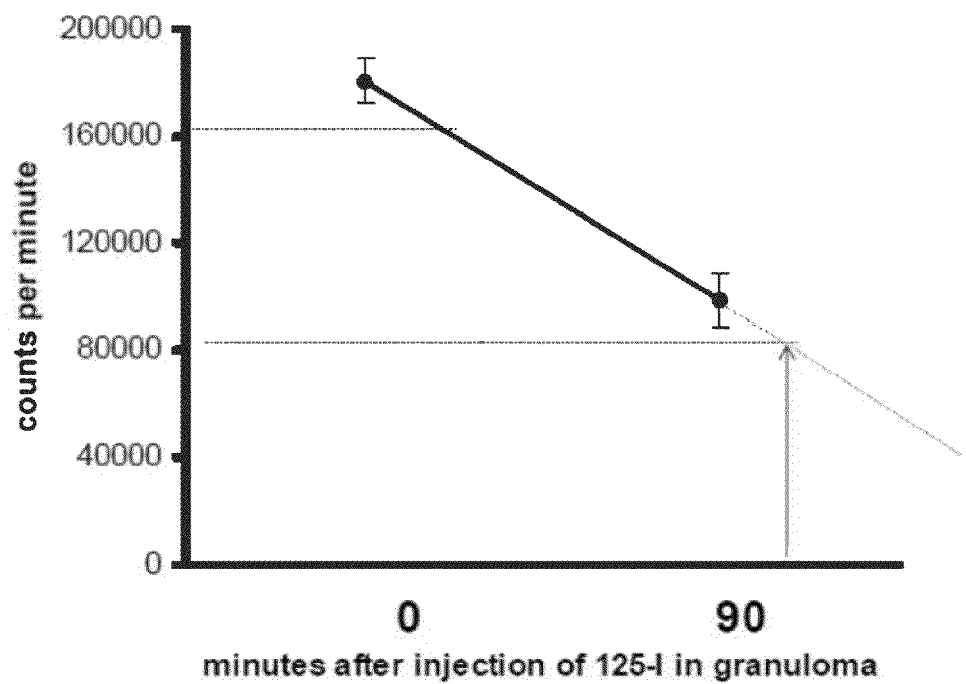
FIG. 2 is a plot of the rate of formation of fluid in the rat granuloma by studying the clearance of injected radioactive sodium iodide (125-I)

An example of how to determine the maximum amount of granuloma fluid that can be harvested or collected is to experimentally perform clearance studies of a radioactive substance injected in the granuloma fluid. For example, two weeks after implantation of apparatus 10 (here a polythene tube), the apparatus 10 contents of fluid were aspirated completely using a syringe and the apparatus 10 was injected with 0.5 ml of sterile saline containing radioactive (125-1) sodium iodide (internal volume of the implanted tube was 0.5 ml). At 90 minutes (considered 0 time) and 180 minutes (considered 90 minutes after 0 time) samples of fluid 26 (granuloma fluid, 0.05 ml) was collected and counted in a gamma counter. FIG. 2 shows the decrease in radioactivity in the granuloma fluid between 0 and 90 minutes. The extrapolated time it took for the radioactivity to decrease to half its earlier value was considered to be the time that 0.25 ml of fluid was made in the granuloma (half of original volume of 0.5 ml). The results from the four granulomas show that it took approx 90 minutes for the rats to make 0.25 ml of granuloma fluid (note that the inside volume of the implanted tube was 0.5 ml) N=4 at each point. Since two apparatuses 10 were implanted in a rat on the two sides, the total possible yield is calculated to be 2*0.25/1.5 (90 minutes converted to hours)*24=8 ml/day. The rat weighed 300 grams and so 2.65% of its body weight in granuloma fluid could be obtained per day. When the methodology is be scaled up and applied successfully in a horse weighing 600 Kg one could obtain 15 kg or 15 L of fluid per day per horse.

The fluid harvested from the granuloma 26 resembles plasma. Electrophoresis of the fluid by SDS-PAGE (gel electrophoresis) clearly showed that the fluid was similar in composition to plasma with respect to the major proteins present in the plasma such as albumin and the globulins (electrophoretogram not presented). Growth factors present in the granuloma fluid are not expected to show up as protein bands on SDS-PAGE because their concentrations are below the sensitivity of the technique. Growth factors are usually assayed by enzyme immunoassay (ELISA) or other immune techniques.

Figure 3:
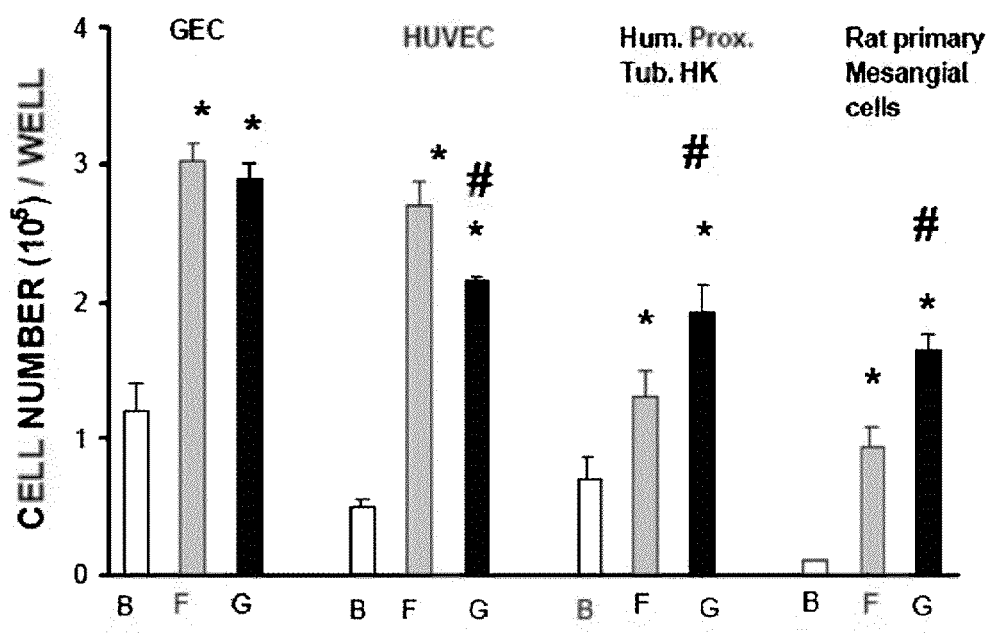
FIG. 3 is a plot illustrating a comparison of the growth promoting effect of media containing 10% granuloma fluid (GF) with conventional media containing either 10% FBS or EGM (a specialized media made by Biowhitaker Inc. for endothelial cells) on four different rat and human cells.

With regards to the biological properties of the granuloma fluid, especially with respect to its abundance in growth factors, four mammalian cells were tested for their growth rates in the granuloma fluid and compared with that observed with the standard FBS containing medium. The cells tested included two derived from the rat (glomerular epithelial cells, GEC and primary rat mesangial cells) and two from human sources (human umbilical vein endothelial cells, HUVEC and human kidney proximal tubular cells, HK). FIG. 3 shows that the basal medium (RPMI) by itself was poor in supporting the growth of these cells. The two media containing either 10% FBS or 10% granuloma fluid were better and equally able to sustain the rat glomerular epithelial cells. In the case of endothelial cells (HUVEC) the specialized media EGM (made by Biowhitaker, NJ, USA) performed better than the granuloma fluid whereas the granuloma fluid was better in supporting the HK and primary mesangial cells (FIGS. 4a-b, 5a-b, 6a-b, 7a-b). It may be noted that compared to FBS, the granuloma fluid better supported the primary mesangial cells, which being immediately derived from an organ are known to be more fastidious in their growth requirements than other cells. Further, granuloma fluid was equal to FBS in differentiating the HUVEC to form capillaries in vitro when grown on a solid matrix (Matrigel®) (FIGS. 8a-b). Overall, these results show that the granuloma fluid is not only a good substitute for FBS for the growth of mammalian cells, but performs better than FBS as an essential ingredient in tissue culture media.

As discussed above, FIG. 3 shows a comparison of the growth promoting effect of media containing 10% granuloma fluid with conventional media containing either 10% FBS or EGM (a specialized media made by Biowhitaker Inc. for endothelial cells) on four different rat and human cells. Cell number was determined by gentian violet staining and measuring the color of gentian violet in a spectrophotometer after de-staining the cells. The white bars (B) is a Basal medium, RPMI. In case of human vein endothelial cells (HUVEC) basal media was EBM. The grey bars (F) are a Basal+10% FBS. In case of HUVEC (F) media consisted of basal EBM+unknown growth factors+2% FBS as recommended by Biowhitaker, Inc. (the combination of the three constituents above is called EGM). The black bars (G) are Basal+10% granuloma fluid. Overall, these results showed that the granuloma fluid performed better than FBS for the culture of mammalian cells.

Figure 4A:
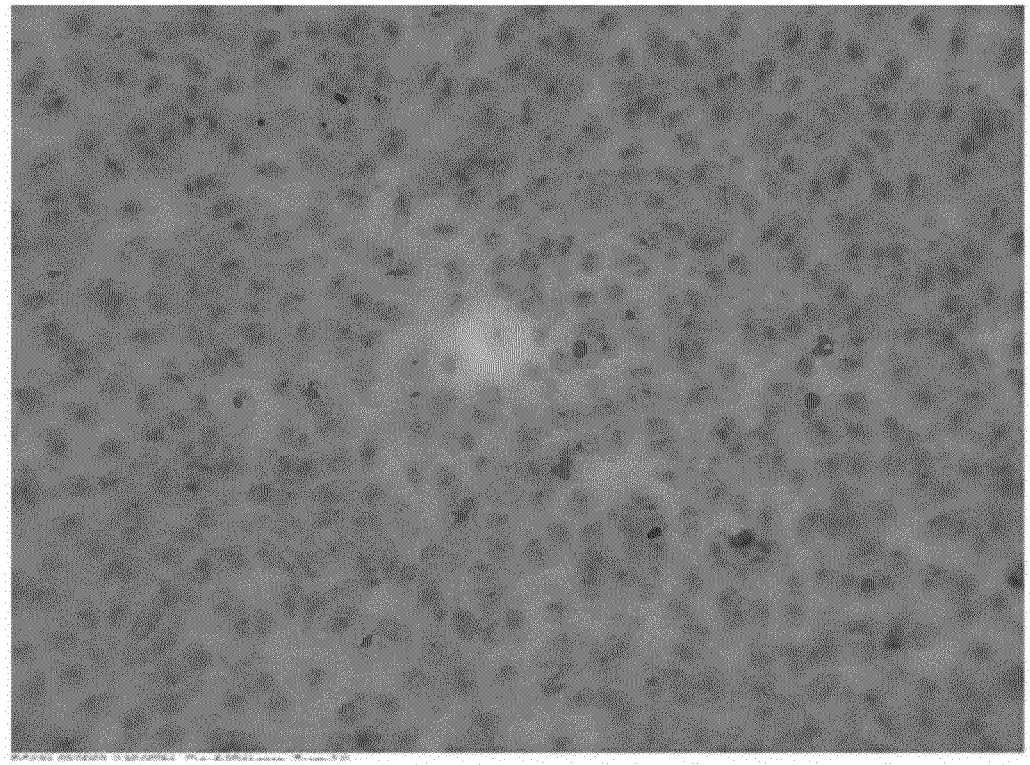
FIGS. 4a-b are microphotographs comparing between FBS (a) and GF (b) in culturing rat glomerular epithelial cells.
Figure 4B:
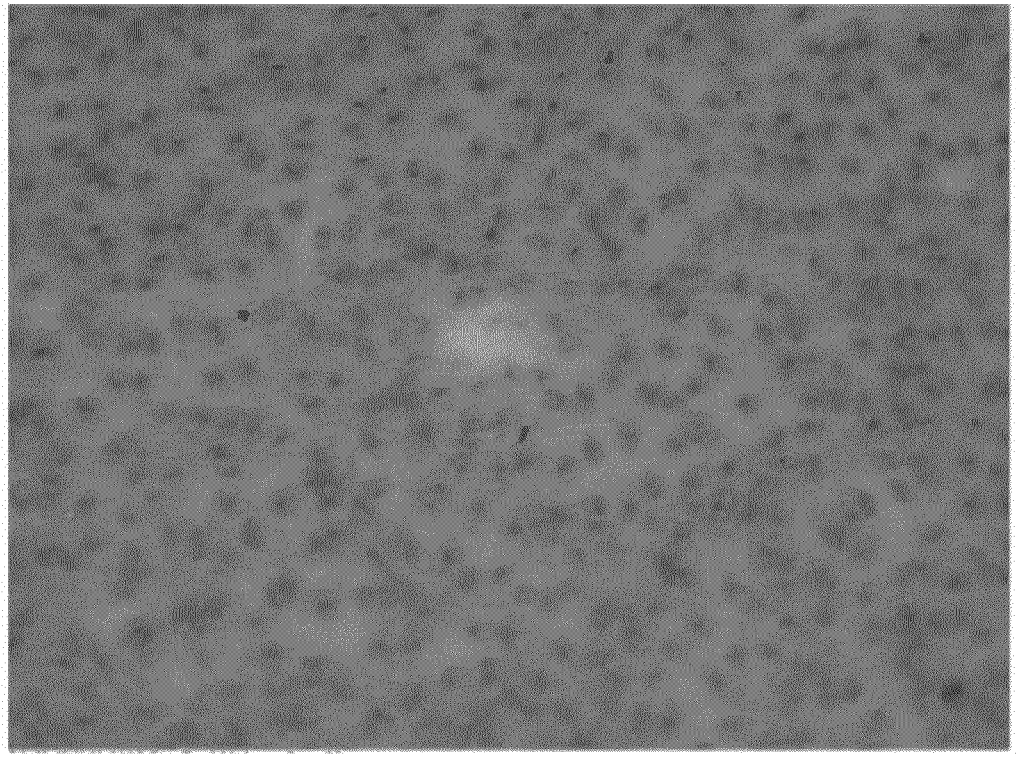

FIGS. 4a-b show a comparison between granuloma fluid and FBS in culturing rat glomerular epithelial cells, noting that FBS and granuloma media are similar in supporting the growth of GEC (250×).

Figure 5A:
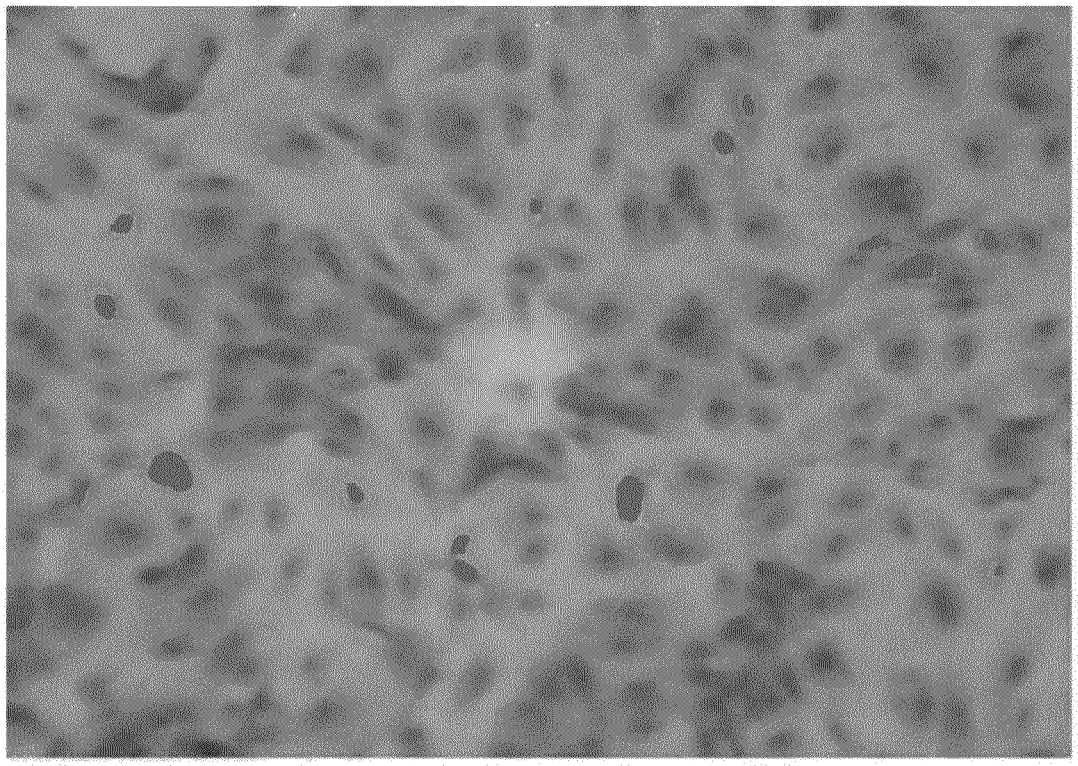
FIGS. 5a-b are microphotographs comparing between EGM (a) and GF (b) in culturing human umbilical vein endothelial cells.
Figure 5B:
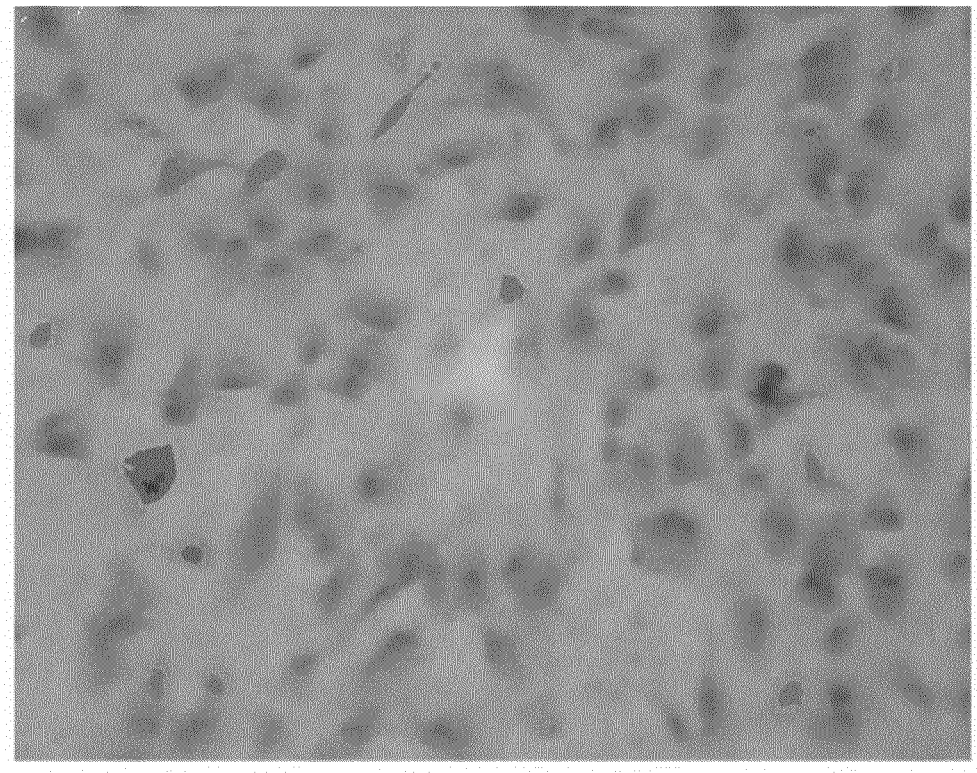

FIGS. 5a-b are microphotographs comparing between granuloma fluid and EGM in culturing human umbilical vein endothelial cells, noting that the commercial media EGM (most optimum media as per supplier) is better than granuloma fluid containing media in supporting HUVEC (250×).

Figure 6A:
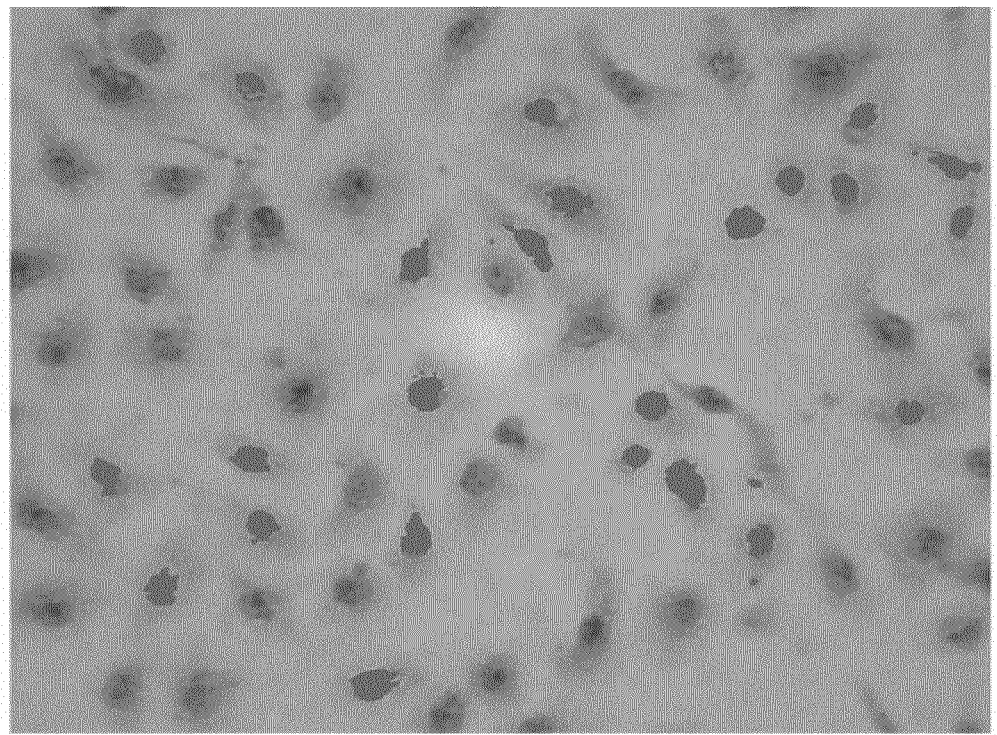
FIGS. 6a-b are microphotographs comparing between FBS (a) and GF (b) in culturing human proximal tubule cells (HK)
Figure 6B:
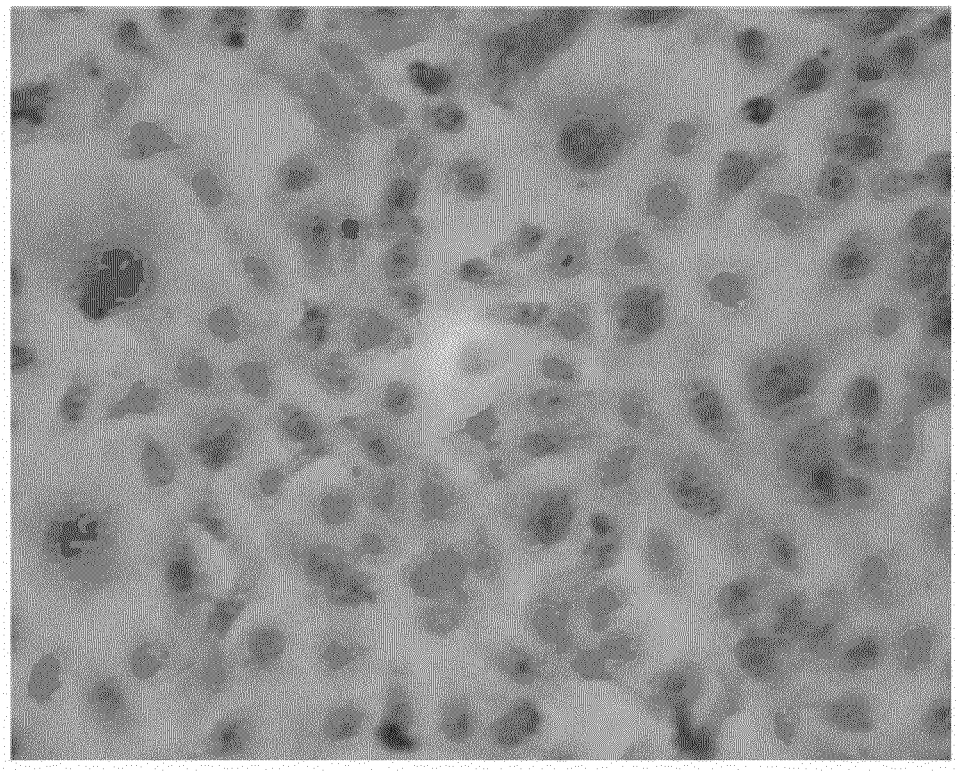

FIGS. 6a-b are microphotographs comparing between granuloma fluid and FBS in culturing human proximal tubule cells (HK), noting that granuloma fluid media is better than FBS media in supporting HK cells (250×).

Figure 7A:
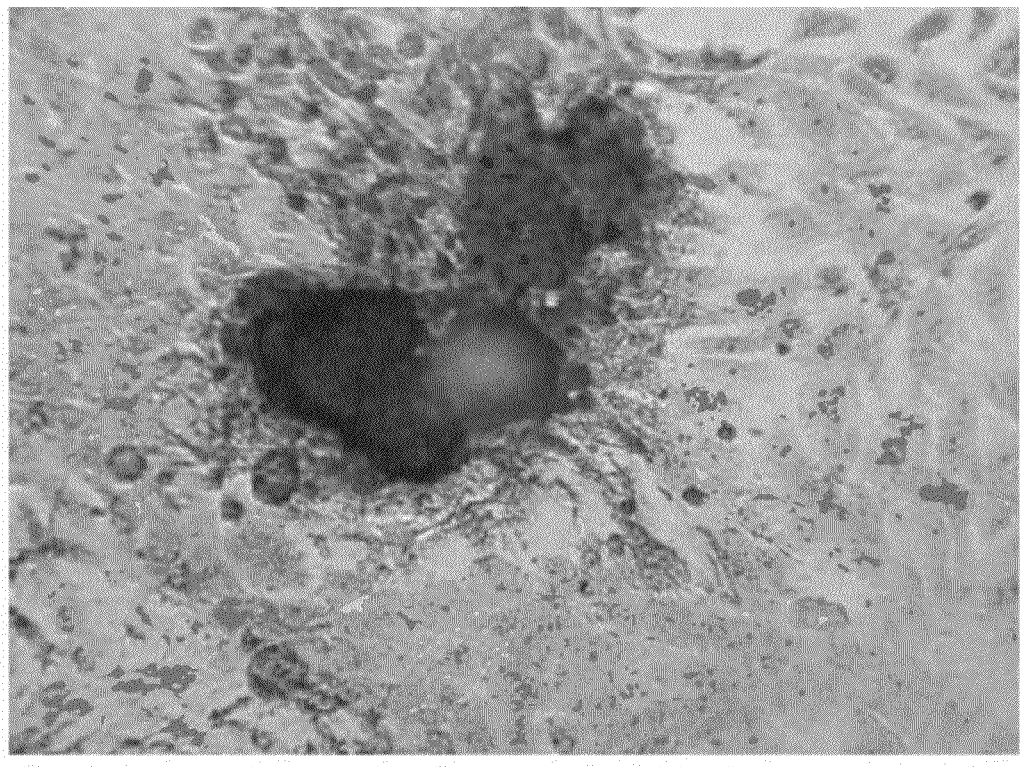
FIGS. 7a-b are microphotographs comparing between FBS (a) and GF (b) in culturing primary mesangial cells from outgrowths of rat glomeruli (dark spots in the picture are remnants of glomeruli)
Figure 7B:
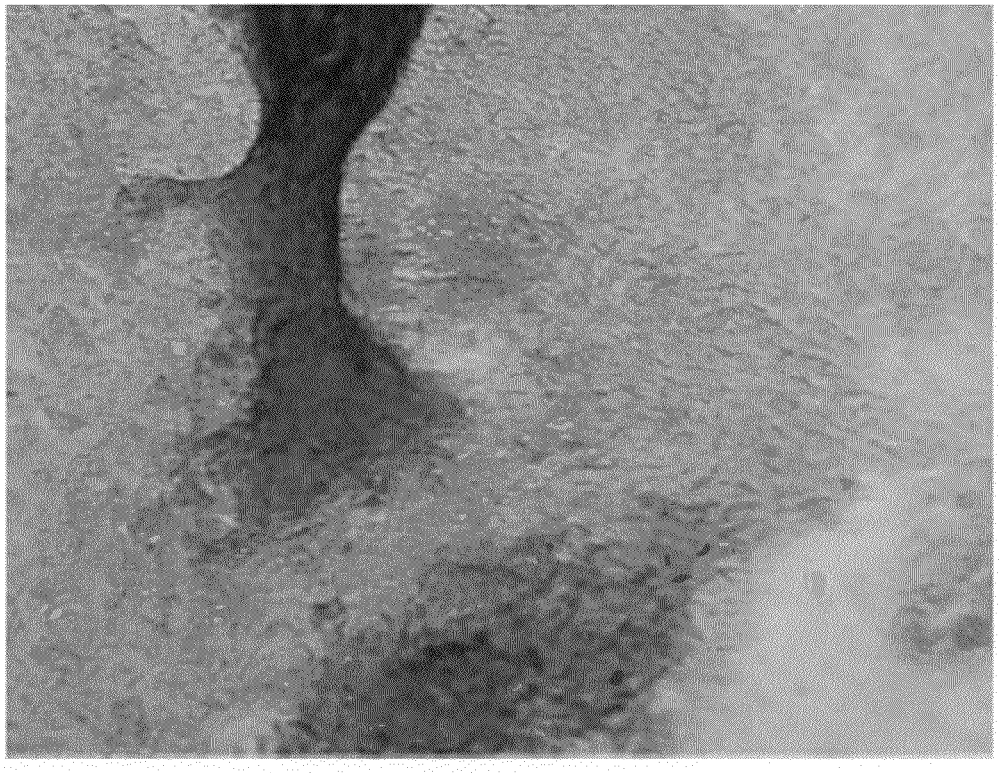
Figure 8A:
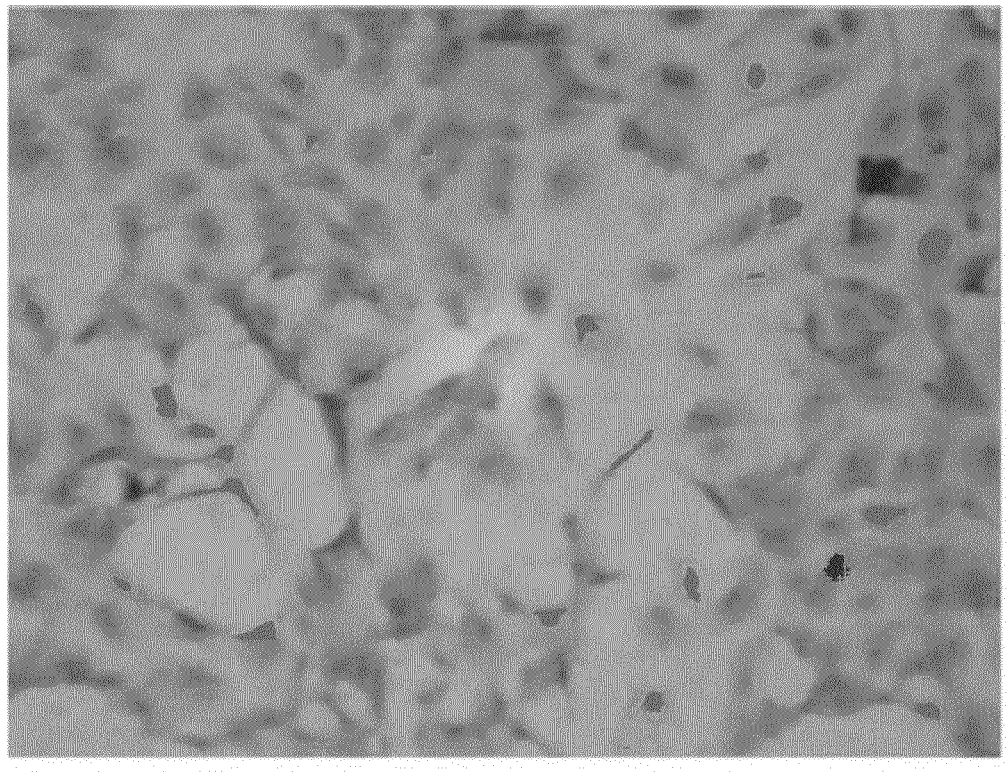
FIGS. 8a-b are microphotographs comparing between EGM (a) and GF (b) in inducing cultured human umbilical vein endothelial cells to form capillaries on Matrigel matrix (in the picture seen as open spaces surrounded by cells)
Figure 8B:
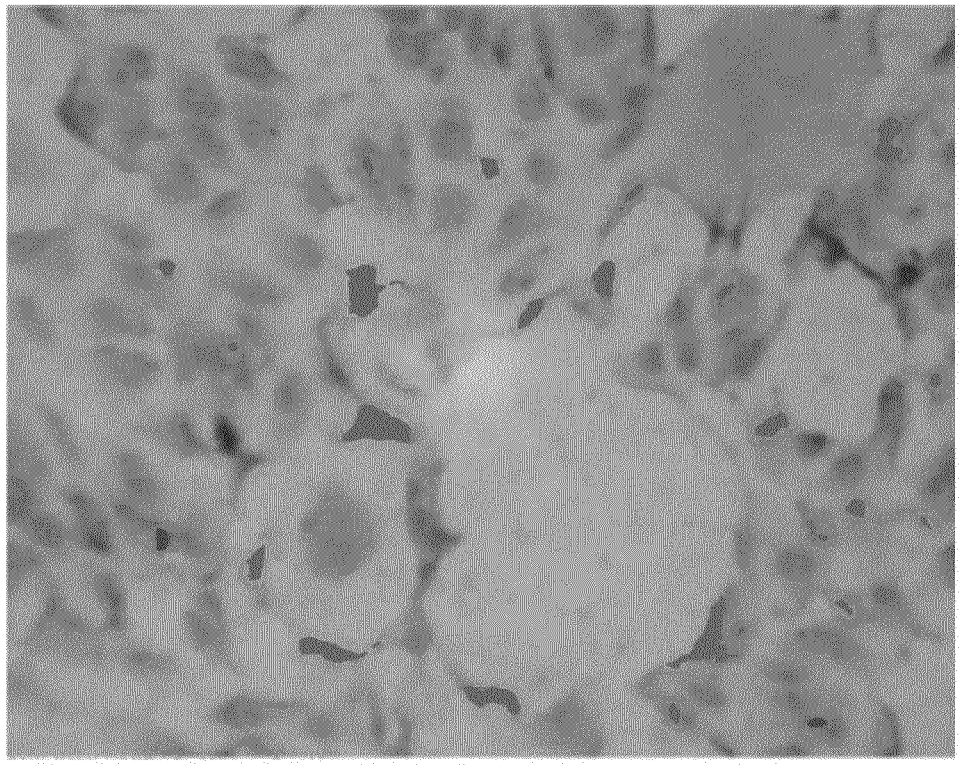

FIGS. 7a-b are microphotographs comparing between granuloma fluid and FBS in culturing primary mesangial cells from outgrowths of rat glomeruli, noting that granuloma fluid media is better than FBS media in supporting primary mesangial cells (100×). The solid red staining bodies are remnants of glomeruli.

FIGS. 8a-b are microphotographs comparing between granuloma fluid and EBM in culturing human umbilical vein endothelial cells on Matrigel matrix to induce capillary formation, noting that both granuloma fluid and EGM media (most optimum media as per supplier) equally induced capillary formation by HUVEC when grown on Matrigel (250×).

Figure 9:
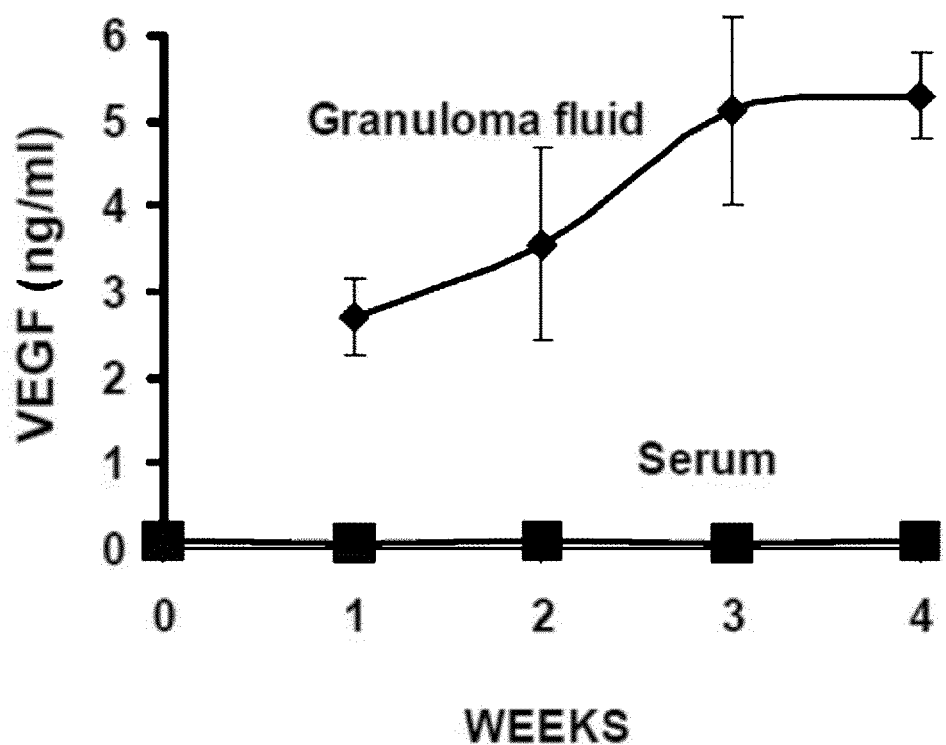
FIG. 9 is a plot of VEGF (vascular endothelial growth factor) concentration in the GF and serum at different times after the implantation of the polythene tube in the rat.

Vascular endothelial growth factor (VEGF) is one of the most powerful growth factors for endothelial and other cells and may be an important growth factor that imparts the special growth-promoting property to the granuloma fluid. VEGF in granuloma fluid is measured by enzyme immunoassay. FIG. 9 shows VEGF concentration in the granuloma fluid and serum at different times after the implantation of the polythene tube in the rat. The fluid could be successfully collected for up to 6 weeks after tube implantation and the VEGF concentration remained at the level seen at week 4 (data of weeks 5 and 6 are not presented). Each point represents the mean of four granuloma fluid or serum samples (limit bars denote standard errors) noting that granuloma fluid is 50 times higher in VEGF concentration than the serum showing the granuloma fluid is a unique fluid which is rich in growth factors. VEGF concentration in FBS has never been measured because there are no available assays for bovine VEGF and therefore a direct comparison with FBS is not possible.

The omentum as well as the subcutaneous tissue activated by a foreign body as described above is rich in adult stem cells. Usually, a 3-7 day old activated tissue has a higher number of stem cells than older activated tissue. The stem cells in the activated tissue were recognized by the presence of stem cell markers (SDF-1a, CXCR4, WT-1, Nanog, Oct-4, PDX-1) (FIG. 13a-f) on the cells, by fluorescence activated cells sorting analysis (FACS) showing CD90, CD59, and CD44 positivity and CD 45 negativity Table 1 (see below), suggesting similarity to mesenchymal stem cells of the bone marrow (in the rat), their ability to produce high amounts of growth factors in culture (VEGF and other growth factors) (FIG. 9), their property of differentiation to other cell types in vitro (adipogenic, osteogenic chondrogenic) (FIG. 16a-f) and their capacity to engraft in injured sites in the body (liver, kidney, skin) following intravenous injection (FIGS. 17a-19). Further support for the presence of stem cells in the foreign-body activated tissues is provided by the observations that when the activated omentum was fused with (a) the injured diabetic pancreas, or (b) injured liver or (c) injured kidney it regenerated new insulin producing cells (FIGS. 10a-b), new liver tissue (FIGS. 11a-b), or new kidney tissue (FIGS. 12a-b), respectively.

Figure 10A:
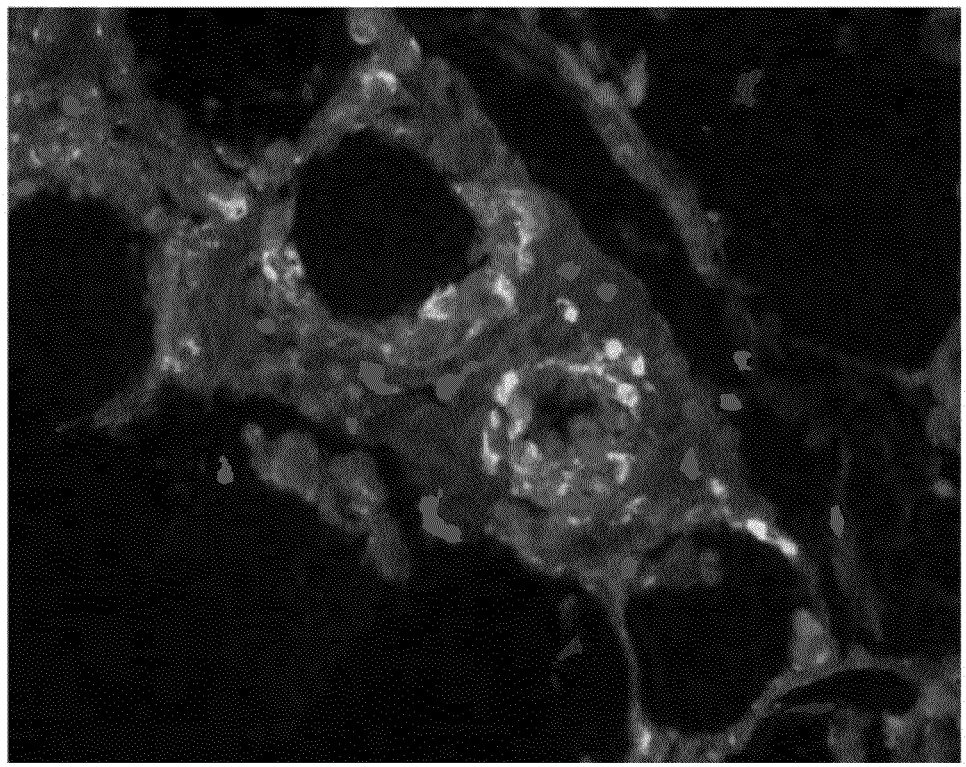
FIG. 10a is a microphotograph of an omentum from the autotransplanted diabetic rats which became normoglycemic. Picture shows niches of insulin positive cells (appearing as white spots) in the cluster of cells surrounding the polydextran particles (polydextran particles do not appear in the picture)
Figure 10B:
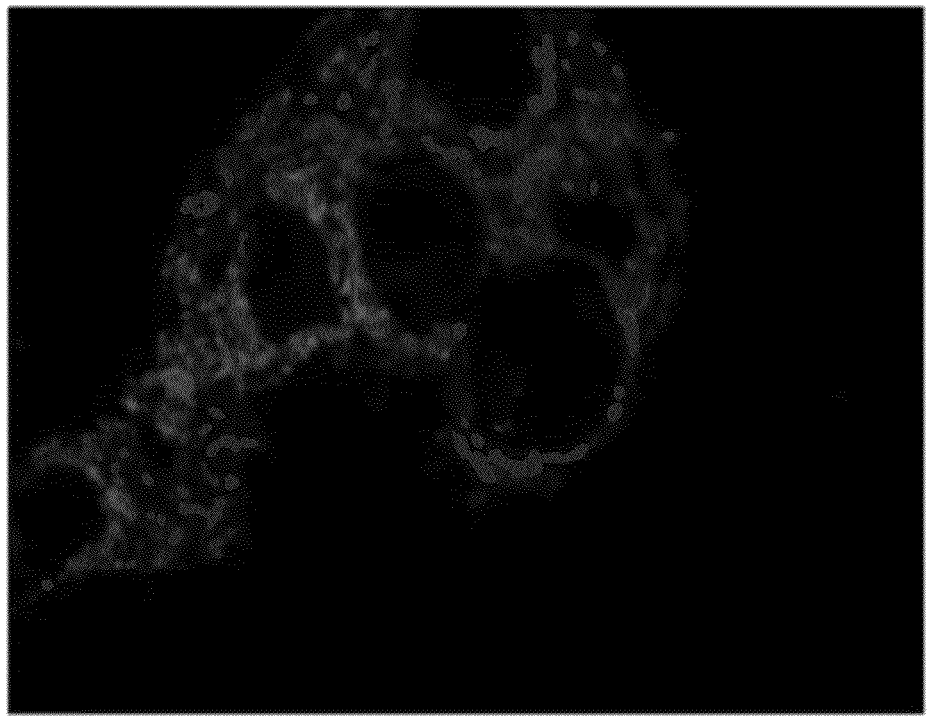
FIG. 10b is a microphotograph of an omentum from diabetic control rats who did not receive the auto-transplant and were negative for insulin producing cells as were omentum from normal control rats and activated omentum alone (absence of white spots in the picture)

With regards in FIGS. 10a-b, detection of insulin positive cells (by immunocytochemical staining) in the omenta of diabetic rats auto-transplanted with their own dispersed pancreas in the peritoneal cavity after activating the omentum by polydextran particles. FIG. 10a illustrates omenta from the autotransplanted diabetic rats which became normoglycemic showed niches of insulin positive cells (appearing green) in the cluster of cells surrounding the polydextran particles. FIG. 10b illustrates omenta from diabetic control rats who did not receive the auto-transplant were negative for insulin producing cells as were omenta from normal control rats and activated omenta alone. Tissues were counterstained with ethidium bromide to highlight cell nuclei. These results showed that diabetic pancreas when placed in activated omentum gave rise to new insulin-producing cells.

Figure 11A:
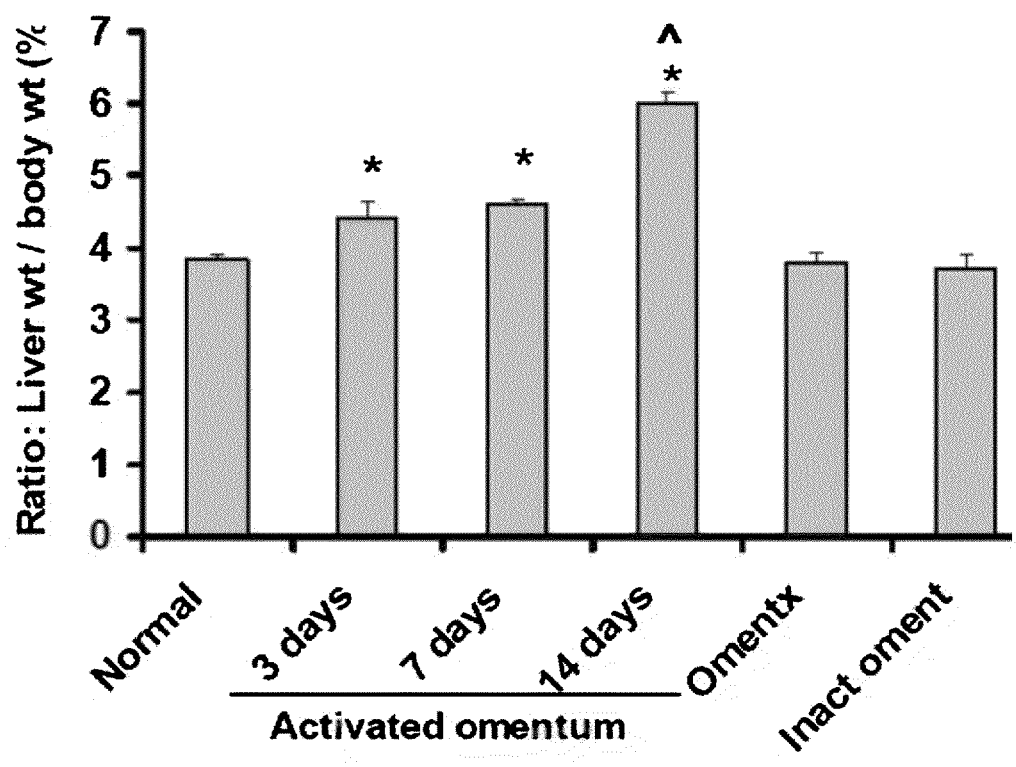
FIG. 11a is a plot of liver mass (as a ratio to body weight) at different times after wounding and fusing of the activated omentum to the wound. 'Omentx' refers to control rats with omentectomy and 'inact omentum' refers to another control group of rats with un-activated omentum. (* denotes statistical difference from normal at P<0.05 and ˆ denotes statistical difference from 7 day at P<0.05)

With regards to FIG. 11a, liver mass (as a ratio to body weight) at different times after wounding and fusing of the activated omentum to the wound is shown. The ratio of liver weight to body weight in normal rats was established to be 3.85±0.07%(n=24). 'Omentx' are rats in which the omentum was removed before liver wounding (n=12) and 'unact oment' are rats in which the liver was wounded but the omentum was un-activated (n=12). The regeneration following wounding and fusion of activated omentum was rapid as by day 3 the liver grew to 110% of original mass. The liver continued to grow, reaching the maximum size of 150% of the original mass by 14 days, after which it stopped growing (28 day data not shown). Number of rats was 15 in case of normal; 6 in each of 3, 7, 14 and 28 day groups. * denotes statistical difference from normal or 'omentx' or 'unact oment' groups at $p<0.05$. ^ denotes statistical difference from day 3 and day 7 groups at $p<0.05$. In regard to 'omentx' and 'unact oment' groups no differences were seen at days 3, 7, 14 and 28 compared to Normal (only day 14 data is shown in the figure; n=3).

Figure 11B:
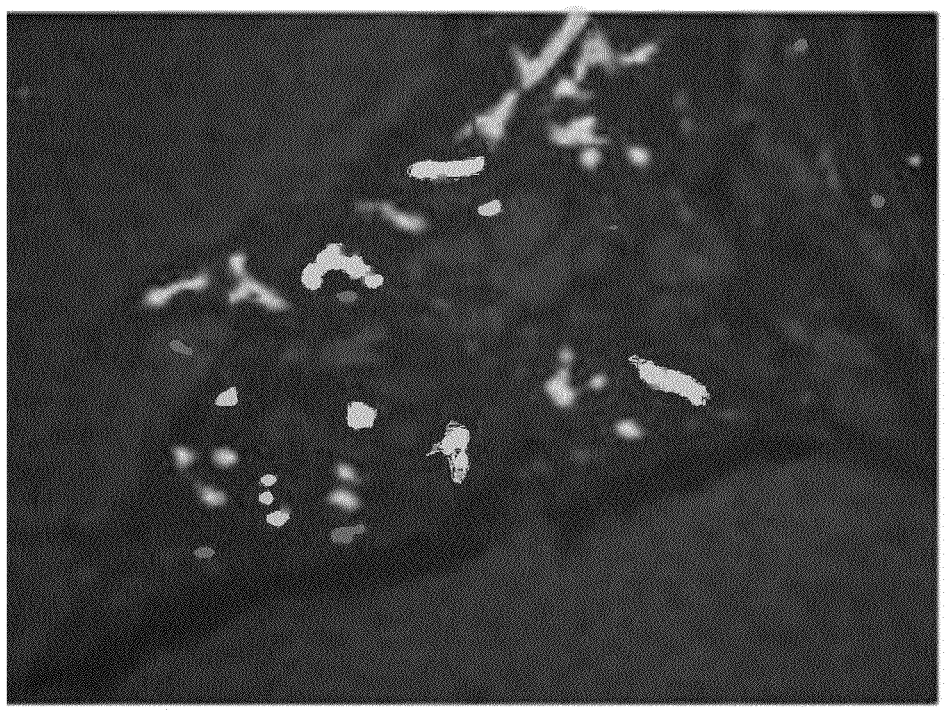
FIG. 11b is a microphotograph of a wedge of omental tissue that adhered to the cut edge of the liver and in which bile ducts (appearing as white structures) containing cytokeratin-19 positive oval cells (stem cells of the liver) are extended.

With regards to FIG. 11b, the wedge of omental tissue is shown adhered to the cut edge of the liver and in which bile ducts containing cytokeratin-19 positive oval cells (stem cells of the liver) are extended. The extra-hepatic proliferation of the oval cells is believed to be responsible for the liver regeneration seen in this model.

Figure 12A:
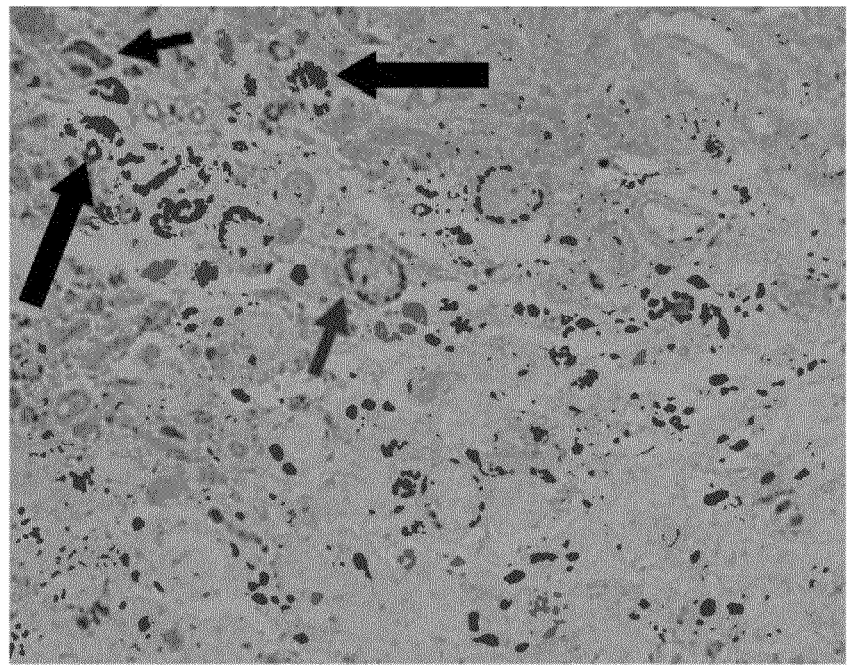
FIG. 12a is a microphotograph of a WT-1 immune stained injured kidney fused to the activated omentum showing the regenerating zone (area of fusion between omentum and kidney) containing structures (stained as small black dots representing cell nuclei) resembling embryonic nephrons two weeks after injury.

With regards to FIG. 12a, WT-1 immune stained injured kidney two weeks after injury and omentum activation shows the regenerating zone (area of fusion between omentum and kidney). The individual WT-1 positive cells seen at 3-7 days (not shown) seemed to have organized into structures that were suggestive of embryonic bodies like renal vesicles (bottom left arrow), comma (top center arrow) and S-shaped (top left arrow) structures, and also glomerular-appearing structures with WT-1 positivity concentrated in the outer margin of the glomerular tuft in the shape of a crown (bottom center arrow), typical of early fetal glomeruli.

Figure 12B:
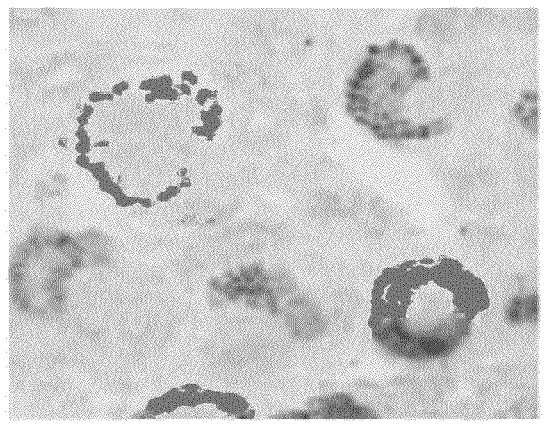
FIG. 12b is a microphotograph of a fetal rat kidney immune-stained for WT-1 shown for comparison of embryonic structures with those found in the adult regenerating kidney.

With regards to FIG. 12b, a fetal rat kidney immune-stained for WT-1 is shown for comparison of embryonic structures with those found in the adult regenerating kidney.

The cells from the activated omentum as well as the subcutaneous tissue could be cultured using Mesenchymal Stem Cell Growth Media with 10% fetal bovine serum. The cells could also be subcultured for several passages without loosing their stem cell characteristics (stem cell markers, secretion of growth factors etc.). Maintaining the cells in culture allows one to freeze the cells for future use.

One example of a method to obtain stem cells from foreign body-activated adult tissues includes the following steps:

a) For activating omental tissue, rats (Sprague-Dawley, 200-250 g) or any other large animal species would be injected with 5 mL or more of polyacrylamide particle slurry (Biogel P-60, 120 µM; Biorad Laboratories, Richmond Calif.) (1:1 in normal saline) intraperitoneally. After 3-7 days the animals would be laparotomized and the expanded omenta would be surgically harvested for culture or single cell preparation.

b) For activating the subcutaneous tissue, rats (Sprague-Dawley, 200-250 g) or any large animal species would be implanted a piece of polyvinyl chloride tubing (in case of rats: L=25 mm, internal diameter=3 mm) (PVC 180 Nalge Nunc International, Rochester, N.Y.) heat-sealed at both open ends in the subcutaneous space at the back of the rats. After 4-10 days the animals would be anesthetized and the tube with the trapped granulation fluid and attached granulation tissue could be surgically harvested for 1) separation of free-floating cells in the fluid (by simple centrifugation at 2000 g for 15 minutes) for immediate use, 2) preparation of stem cells from the attached solid granulation tissue by making a single cell preparation (for immediate use—see example below) or by culturing (for expanding the cell number and for use over long-term).

c) Omental tissue activated by a foreign body as above is a good starting material for stem cell preparation as it is rich in stem cell content as shown by the expression of stem cell markers (FIGS. 13a-f).

d) For culturing stem cells from the activated omentum (or subcutaneous tissue) obtained above, the harvested tissue would be placed aseptically in Mesenchymal Stem Cell Growth Media (MSCG) supplemented with growth factors supplied by the manufacturer (Lonza; WalkersvilleA1D, USA), glutamine, antibiotics, and 10% fetal bovine serum. The tissue would be gently chopped, scrapped over a No. 60 stainless steel sieve (pore size approx 300 μM) and treated with collagenases enzyme to make a single cell preparation. The cells at this stage could be used as 'freshly-isolated' stem cells for repair and treatment or alternatively, cultured for future use as follows: The cells will be suspended in fresh MSCGM and placed in culture dishes that are incubated in 5% $CO_2$-95% air environment at 37° C. for 7-10 days without changing the media. After the cells reach approx. 80% confluency they will be removed from the dish by trypsin treatment and re-cultured on three fresh dishes (passage 1; split ratio 1:3) for expansion. The cells could be multiplied by passaging them for up to 10 passages (FIG. 14a-b).

With regards to FIGS. 13a-f, microphotographs are shown of rat omentum activated with polydextran particles and immunostained for adult stem cell and embryonic pluripotent markers shown by the arrows of strong immuno-reactivity for WT-1 (FIG. 13a), SDF-1a (FIG. 13b), and CXCR 4 (adult stem cell markers) (FIG. 13c) and to Nanog (FIG. 13d), Oct-4 (FIG. 13e) and SSEA-1 (embryonic markers) (FIG. 13f). Reactivity for all markers (except WT-1) was limited to the cells immediately surrounding the polydextran particles in the activated omentum (spaces occupied by the polydextran particles are indicated by arrows). WT-1 positive cells (staining is nuclear as expected) were exceptionally in the stroma of the tissue and not in the location immediately surrounding the polydextran particles. As expected normal adult rat tissues like kidney and liver were negative for the stem cell markers (not shown).

With regards to FIG. 14a, a primary culture of omental cells cultured from omentum tissue activated by polydextran particles for 7 days is shown. After 4-5 days in culture, cells that originally clustered around the polydextran particles started to attach to the dish and multiply (one such particle surrounded by attached cells is shown in the middle of the field). The cell morphology and phenotype was like those of smooth muscle cells and the bone-marrow derived human mesenchymal stem cells. Similar cultures were obtained from 1-day and 4-day activated omenta (not shown). Activated omentum older than 2 weeks was difficult to culture as the cells did not attach or multiply as readily as the cells from younger omenta (not shown).

With regards to FIG. 14b, passage 3 cells show robust growth. The cells could be maintained in culture for more than 10 passages.

Characterization of cultured stem cells from activated omentum (and also subcutaneous tissue) can be determined by 1) expression of pluripotent markers and mesenchymal stem cell surface markers (FIG. 15a-f), 2) their ability to transform to adipogenic, chondrogenic and osteogenic cell phenotypes in vitro (FIG. 16a-f)) and 3) their ability to secrete high levels of vascular endothelial growth factor (VEGF) (FIG. 9).

Now turning to FIGS. 15a-f, the stem cell markers present in the original tissue continue to be expressed in cultured cells for up to 10 passages showing that the cultured cells were as potent as the original tissue. Further, fluoroscein-activated cell sorting (FACS analyses) for cluster of differentiation markers (CD) showed that the cells isolated from the foreign body activated adult tissues (omentum and subcutaneous) were of bone marrow mesenchymal type (CD90, 44, 59+ and CD 45−; see Table 1 below) and not hematopoietic type. Hematopoietic cells are always CD 45 positive.

TABLE 1

| Cells | CD 44 | CD 45 | CD 59 | CD 90 |
| --- | --- | --- | --- | --- |
| Omental | high+ | neg | high+ | high+ |
| Subcut. | low+ | neg | low+ | high++ |
| BM | low+ | neg | low+ | high++ |

BM: bone marrow mesenchymal cells

Primary cultures of omental cells stained for adult and embryonic stem cell markers. Cultured omental cells stained positive for adult stem markers WT-1 (nuclear), CXCR4 (nuclear), and SDF-1a (cytoplasmic) as seen in the intact tissue previously (FIGS. 15a-c; compare with intact omentum tissue staining in FIGS. 13a-c). Also, as seen in the intact omental tissue (see FIGS. 13d-e), the cultured cells stained strongly positive for Nanog (FIG. 15d; nuclear) and Oct-4 (FIG. 15e; cytoplasmic). Cell staining was negative in the absence of first antibody (FIG. 15f; control). Unlike the SSEA-1 positive staining seen in the omental tissue (FIG. 13f) the cultured omental cells were negative for SSEA-1 (not shown) suggesting that even though the cultured cells largely maintained their stem cell property there was a slight alteration of phenotype upon culture.

Now turning to FIGS. 16a-f, cultured subcutaneous-tissue derived stem cells when placed in specialized medium differentiated in vitro to adipogenic, chondrogenic and osteogenic cell types. Adipogenic (FIGS. 16a, 16d), osteogenic (FIGS. 16b, 16e), and chondrogenic (FIGS. 16c, 16f), differentiation of subcutaneous derived stem cell cultures by incubation of cells in specialized (tissue-specific) medium. In FIGS. 16a-c, arrows show differentiated adipocytes, osteocytes, chondrocytes stained with oil Red O, alizarin red and alcian blue respectively containing either lipid droplets stained red (FIG. 16a), or mineral deposits stained brown (FIG. 16b) or proteoglycans stained blue (FIG. 16c). Inset in FIG. 16a shows adipocytes containing lipid droplets stained red at higher magnification. FIGS. 16d-f show control cultures grown with normal growth medium stained negative for respective markers.

Table 2 illustrates that the cultured omental stem cells and those cells obtained from the subcutaneous granulation tissue produced up to 10-20 fold higher amounts of VEGF than commonly cultured cells from other adult tissues (glomerular epithelial cells and primary mesangial cells), which are non-stem cell lines obtained from rat kidneys.

TABLE 2

| Cultured cell | VEGF synthesis rate (pg/hr/million cells) |
|---|---|
| Omental stem cells | 322 ± 22 |
| Subcutaneous granulation tissue stem cells | 230 ± 15 |
| Glomerular epithelial cells* | 17.6 ± 2.4 |
| Primary mesangial cells** | 32.1 ± 3.8 |

*A cell line of glomerular epithelial cell originally obtained from Kreisberg (Kreisberg et al. Isolation and characterization of rat glomerular epithelial cells in vitro. Kidney International 14: 21-30, 1978.
**VEGF synthesis rate was determined in cultured mesangial cells in a previous publication (Singh et al. Vascular factors in glomerular mesangial cells and diabetic glomeruli. Changes in vascular factors impair endothelial cell growth and matrix. Laboratory Investigation 84: 597-606, 2004.

Now turning to FIGS. 17a-c, 18a-b, and 19 to illustrate a test for 'stemcellness' of cultured omental stem cells by their ability to engraft to injured sites in animals. When fluorescence labeled cultured omental (or subcutaneous) stem cells (or other adult tissue cells similarly labeled) were injected subcutaneously or intravenously they engrafted to injured skin, kidney and liver of rats and not to uninjured sites of the rat. Cells similarly prepared from normal adult tissues (non-stem cells) did not engraft to injured sites, confirming the 'stemcellness' of cells isolated from foreign body activated tissues.

With regards to FIGS. 17a-c illustrating the migration of cultured omental cells to a skin wound healing site. FIG. 17a are cultured omental cells metabolically labeled with a vital fluorescent dye before injection in rats, noting a suspension of cultured omental cells (light spots) uniformly labeled with the fluorescent dye before injection. FIGS. 17b and 17c are cryo-sections of the wound tissue 24 hours after injection of either fluorescein labeled cultured omental cells (FIG. 17b) or labeled adult kidney cells (control, non-stem cell) (FIG. 17c) in the vicinity of the granulation tissue. FIG. 17b shows the migration and engraftment of the injected omental stem cells in the wound tissue. FIG. 17c show the labeled adult kidney control cells remained at the injection site without migrating to the wound tissue.

Now turning to FIGS. 18a-b illustrating the migration of cultured omental cells to injured kidney. FIG. 18a shows an ischemic left kidney after labeled omental cells (light contrast areas illustrated by the arrows) were injected systemically in the rat with unilateral ischemic injured kidney (3 days after injury). The cells migrated to the injured tubules by 24 hours, appearing to attach to the injured tubules. Also the cells appeared to have altered from their original round shape to more elongated forms suggesting their participation in the healing process. FIG. 18b shows that the non-ischemic contralateral kidney did not contain fluorescent cells suggesting that omental cells specifically recognized injured sites in the body. For contrast, tissues were counterstained with ethidium bromide to stain cell nuclei red.

Now turning to FIG. 19 illustrating a liver tissue 3 days after a resection injury and 24 hours after injection of fluorescent labeled cultured omental cells showing engraftment of the injected cells (lighter contrast) to the growing liver. A white line drawn in the figure represents the border between the native and regenerating sections of the liver. No green fluorescent cells were visible in the native liver. The section was counterstained with ethidium bromide to highlight cell nuclei.

One embodiment of the present invention is a product of the above process wherein the product is a regenerated tissue produced either in the skin or in the omentum by a foreign body, offering a source of stem cells. The product can be used in:

(i) generally for medical, veterinary and cosmetic application either as an intact tissue or as individual stem cells extracted from either the fluid (by centrifugation) or from the intact tissue (by enzymatic treatment) or as cultured stem cells (by culturing individual stem cells) or as;

(ii) as a piece of tissue for organ repair (heart valve, joint, intervertebral disc etc.), as a surgical filler tissue for filling tissue lost from ischemic or other injury, or as an artificial skin in cases of third degree burns, or as a piece of detached pedicle for placing on injured organs (example: spinal cord) to induce angiogenesis (new blood vessel formation) and accelerate wound healing;

(iii) injections (local or systemic) containing freshly extracted individual cells or cultured stem cells for treatment of acute and chronic diseases; or (iv) manufacture of purified growth factors from the culture medium of cultured cells.

Another embodiment of the present invention is a product of the above process wherein the product is a fluid that is harvested from the device. The product can be used in:

(i) generally for medical, veterinary and cosmetic use;

(ii) topical and systemic formulations for cosmetic use as anti-aging injections, creams and lotions;

(iii) dressings for accelerating healing of skin injuries and surgical wounds;

(iv) a treatment of acute and chronic diseases many of which respond to growth factors;

(v) as an additive in culture medium to substitute fetal bovine serum for culture of mammalian cells; or (vi) as a starting material for isolating and purifying growth factors for medical use.

Another product of the present invention is the granulation fluid being packaged in a powdered form. The advantage of formulating the fluid in the powdered form is that it is biologically stable at ambient temperature and so it does not have to be stored frozen to maintain its biological activity. The powdered form permits the use of the fluid in small doctor's and veterinarian's office as well in remote field situations where access to a freezer may not be available.

The powdered form of the granulation fluid is prepared by freeze drying the fluid (process called lyophilization) in, for example, a lyophilizer, at the ratio of 1 mL granulation fluid yields approximately 50 milligrams of granulation powder (containing mostly albumin and growth factors). At the time of use the doctor or other attending personnel will re-constitute the fluid by adding a measured amount of sterile water (water grade used will be 'water for injection' (WFI)) with the help of a syringe and a needle from a separate vial (supplied with the preparation) to the vial containing the powdered preparation, shaking the vial to re-suspend the preparation, waiting for a few minutes to allow complete dissolution and finally taking the preparation in the injection syringe for injection in the patient.

One example of the powdered formed is used for an injection prepared for a dog knee joint. The veterinarian will be supplied with two vials, one containing 50 milligrams of proteins including albumin and growth factors obtained from freeze dried granulation fluid and the other containing 2 mL of WFI water. The veterinarian will obtain 1 mL of water from the water vial using a syringe and needle and transfer to the vial containing the powder. The vial will be gently shaken (to avoid frothing) and let stand for 1-2 minutes to allow the powder to be completely dissolved. The dissolved powder should be a free of turbidity. The clear solution will then be taken in a 1 mL syringe and injected into the knee joint of the dog patient.

Another example of the powdered form is for an injection prepared for a horse knee joint. The veterinarian will be supplied with two vials, one containing 250 milligrams of proteins including albumin and growth factors obtained from freeze dried granulation fluid and the other containing 10 mL of WFI water. The veterinarian will obtain 5 mL of water from the water vial using a syringe and needle and transfer to the vial containing the powder. The vial will be gently shaken (to avoid frothing) and let stand for 1-2 minutes to allow the powder to be completely dissolved. The dissolved powder should be a free of turbidity. The clear solution will then be taken in a 5 mL syringe and injected into the knee joint of the horse patient.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method for treating a condition associated with damaged or diseased tissue in a patient, the method comprising administering to the patient a therapeutically effective amount of fluid isolated from a granuloma induced by a foreign body implanted under the skin or in the omentum of a live mammal, wherein the fluid so obtained contains albumin, globulins and at least 2 ng/mL of vascular endothelial growth factor (VEGF), and exceeds FBS in potency for promoting the growth of HK and primary mesangial cells in culture media, and the method results in an improvement in the patient's condition.

2. The method of claim 1, wherein the method results in the repair or regeneration of at least a portion of the damaged or diseased tissue.

3. The method of claim 1, wherein the damaged or diseased tissue comprises arthritic tissue.

4. The method of claim 1, wherein the damaged or diseased tissue comprises organ tissue.

5. The method of claim 1, wherein the damaged or diseased tissue comprises joint tissue, intervertebral disc tissue, skin, kidney tissue, liver tissue, heart tissue, spinal cord tissue, surgically wounded tissue, or a combination thereof.

6. The method of claim 5, wherein the damaged or diseased tissue comprises joint tissue.

7. The method of claim 6, wherein the joint tissue is knee joint tissue.

8. The method of claim 6, wherein the patient is a dog.

9. The method of claim 6, wherein the patient is a horse.

10. The method of claim 1, wherein the granuloma fluid is administered topically.

11. The method of claim 1, wherein the granuloma fluid is administered systemically.

12. The method of claim 11, wherein the granuloma fluid is administered by injection.

13. The method of claim 11, wherein the granuloma fluid is administered intravenously.

14. The method of claim 11, wherein the granuloma fluid is administered subcutaneously.

15. The method of claim 11, wherein the granuloma fluid is administered intraperitoneally.

16. The method of claim 1, wherein the granuloma fluid is harvested from a pig, cow, horse, sheep, dog, rat, or rabbit.

17. The method of claim 1, wherein the granuloma fluid is obtained by reconstituting a solid form of the granuloma fluid.

18. The method of claim 1, wherein the granuloma fluid is isolated by centrifugation.

19. The method of claim 1, wherein the patient is a human, horse or dog.

20. The method of claim 1, wherein the patient is a human.

21. The method of claim 1, wherein the patient is a horse.

22. The method of claim 1, wherein the patient is a dog.

23. A method for treating arthritis in a patient, the method comprising administering to the patient a therapeutically effective amount of fluid isolated from a granuloma induced by a foreign body implanted under the skin or in the omentum a live mammal, wherein the fluid so obtained contains albumin, globulins and at least 2 ng/mL of vascular endothelial growth factor (VEGF), and exceeds FBS in potency for promoting the growth of HK and primary mesangial cells in culture media, and the method results in an improvement of the arthritic condition.

24. The method of claim 23, wherein the method comprises treating an arthritic joint.

25. The method of claim 24, wherein the joint is a knee joint.

26. The method of claim 23, wherein the granuloma fluid is obtained by reconstituting a solid form of the granuloma fluid.

27. The method of claim 26, wherein the granuloma fluid is harvested from a horse.

28. The method of claim 27, wherein the patient is human.

29. The method of claim 23, wherein the granuloma fluid is isolated by centrifugation.

30. The method of claim 29, wherein the granuloma fluid is harvested from a horse.

31. The method of claim 30, wherein the patient is human.

32. The method of claim 23, wherein the patient is a human, horse or dog.

33. The method of claim 23, wherein the patient is a human.

34. The method of claim 23, wherein the patient is a horse.

35. The method of claim 23, wherein the patient is a dog.

* * * * *